United States Patent
Kim et al.

(10) Patent No.: US 9,782,469 B2
(45) Date of Patent: Oct. 10, 2017

(54) ANTI-INFLAMMATORY, SKIN-REGENERATIVE, WHITENING, ANTIOXIDANT, OR WOUND-HEALING COMPOSITION CONTAINING CULTURE MEDIUM OF ADSC-T CELLS IN WHICH T-ANTIGEN IS INTRODUCED INTO ADIPOSE-DERIVED STEM CELL AS ACTIVE INGREDIENT

(71) Applicant: Changwon National University Industry Academy Cooperation Corps, Gyeongsangnam-Do (KR)

(72) Inventors: Dongwan Kim, Busan (KR); Han Na Park, Gyeongsangnam-Do (KR); Gyu Bin Kim, Gyeongsangnam-Do (KR)

(73) Assignee: CHANGWON NATIONAL UNIVERSITY INDUSTRY ACADEMY COOPERATION CORPS, Gyeongsangnam-Do (KR)

( * ) Notice: Subject to any disclaimer, the term of this patent is extended or adjusted under 35 U.S.C. 154(b) by 0 days.

(21) Appl. No.: 14/785,265

(22) PCT Filed: Aug. 29, 2013

(86) PCT No.: PCT/KR2013/007769
§ 371 (c)(1),
(2) Date: Oct. 16, 2015

(87) PCT Pub. No.: WO2014/171593
PCT Pub. Date: Oct. 23, 2014

(65) Prior Publication Data
US 2016/0074499 A1    Mar. 17, 2016

(30) Foreign Application Priority Data

Apr. 19, 2013 (KR) .................. 10-2013-0043527
Apr. 19, 2013 (KR) .................. 10-2013-0043536

(51) Int. Cl.

| | | |
|---|---|---|
| *C12N 5/0775* | (2010.01) | |
| *A61K 35/28* | (2015.01) | |
| *A61K 39/12* | (2006.01) | |
| *A61Q 19/02* | (2006.01) | |
| *A61K 8/98* | (2006.01) | |
| *A61K 8/64* | (2006.01) | |
| *A61Q 19/08* | (2006.01) | |
| *C12N 7/00* | (2006.01) | |
| *A23L 33/10* | (2016.01) | |
| *A61K 39/00* | (2006.01) | |

(52) U.S. Cl.
CPC .............. *A61K 39/12* (2013.01); *A23L 33/10* (2016.08); *A61K 8/64* (2013.01); *A61K 8/981* (2013.01); *A61K 35/28* (2013.01); *A61Q 19/02* (2013.01); *A61Q 19/08* (2013.01); *C12N 5/0667* (2013.01); *C12N 7/00* (2013.01); *A23V 2002/00* (2013.01); *A61K 2039/515* (2013.01); *A61K 2039/5156* (2013.01); *A61K 2800/85* (2013.01); *C12N 2502/00* (2013.01); *C12N 2510/04* (2013.01); *C12N 2710/22033* (2013.01); *C12N 2710/22034* (2013.01)

(58) Field of Classification Search
CPC .............. C12N 5/0667; C12N 2502/00; C12N 2510/04; A61K 35/28
See application file for complete search history.

(56) References Cited

U.S. PATENT DOCUMENTS

2006/0147430 A1    7/2006   Sayre et al.
2009/0304654 A1   12/2009   Lue et al.

FOREIGN PATENT DOCUMENTS

| KR | 10-2009-0073658 | 7/2009 |
|---|---|---|
| KR | 10-2013-0021793 | 3/2013 |
| KR | 10-2014-0125943 | 10/2014 |
| KR | 10-2014-0125945 | 10/2014 |

OTHER PUBLICATIONS

Fedele, et al., Bordetella Pertussis-Infected Human Monocyte-Derived Dendritic Cells Undergo Maturation and Induce Th1 Polarization and Interleukin-23 Expression, Infection and Immunity, 2005, 73:3:1590-1597.
McKenzie, et al., Understanding the IL-23-IL-17 Immune Pathway, Trends in Immunology, 2006, 27:1:17-23.
Vane, et al., Inducible Isoforms of Cyclooxygenase and Nitric-Oxide Synthase in Inflammation, Proc. Natl. Acad. Sci., 1994, 91:2046-2050.
Jung, Hair Growth Promoting Effect of Culture Medium of Primary and Immortalized Adipose-Derived Stem Cells (English Abstract on p. 36-37).

*Primary Examiner* — Daniel C Gamett
(74) *Attorney, Agent, or Firm* — Blank Rome LLP

(57) ABSTRACT

The present invention relates to an anti-inflammatory, skin-regenerative, whitening, antioxidant, or wound-healing composition containing a culture medium of adipose-derived stem cell-T (ADSC-T) cells as an active ingredient, in which T-antigen is introduced into an adipose-derived stem cell. The culture medium of ADSC-T cells, according to the present invention, has remarkable effects for treating or inhibiting inflammation by alleviating atopic dermatitis, which is an autoimmune disease, and inhibiting NF-κB activities through an increase of an Iκbα expression. Additionally, the culture medium, according to the present invention, exhibits: excellent skin regenerative effects by having effects of enhancing skin collagen elasticity and reducing wounds, in a collagen culture; excellent skin whitening effects by inhibiting tyrosinase activities and melanin production; and excellent anti-oxidation effects by inhibiting DPPH radical activities. Furthermore, the present invention has remarkable wound-healing effects by enhancing cell mobility of fibroblast, and is thus useful for anti-inflammation, skin-regeneration, whitening, anti-oxidation, or healing wounds.

10 Claims, 11 Drawing Sheets

[Fig. 1]
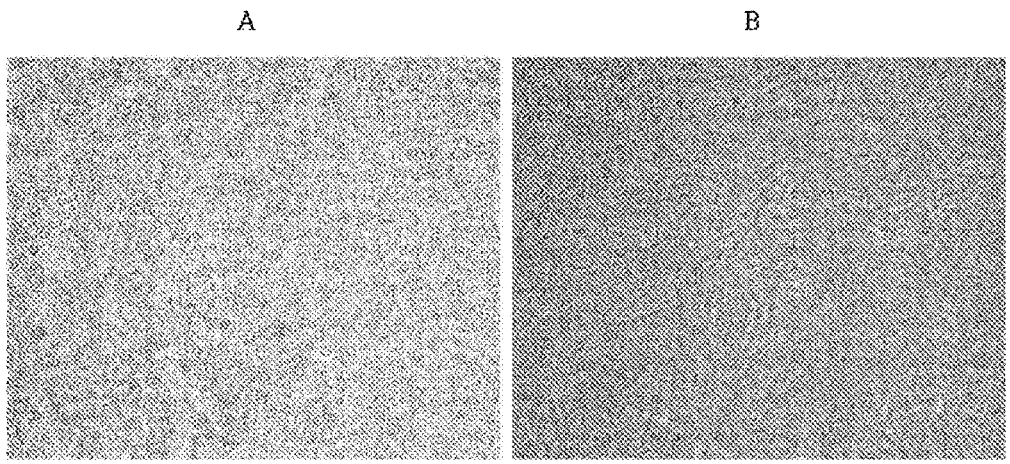
[Fig. 2]
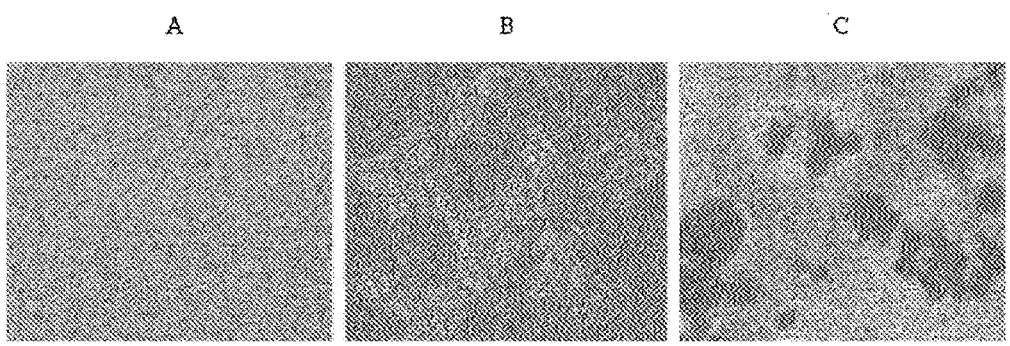
[Fig. 3]
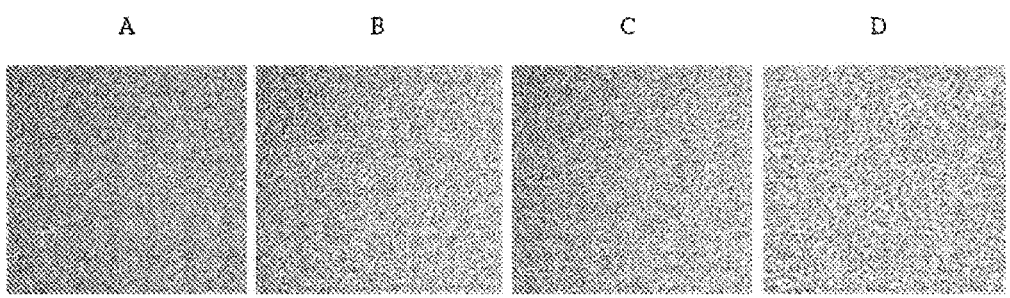

[Fig. 4]
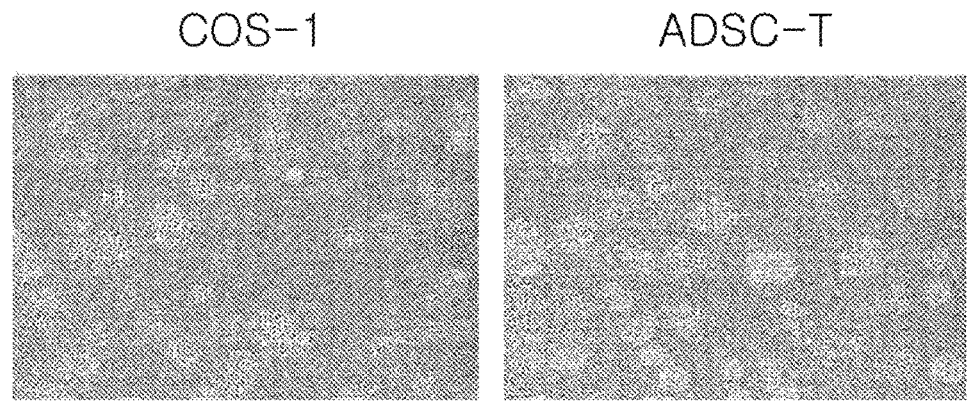
[Fig. 5]
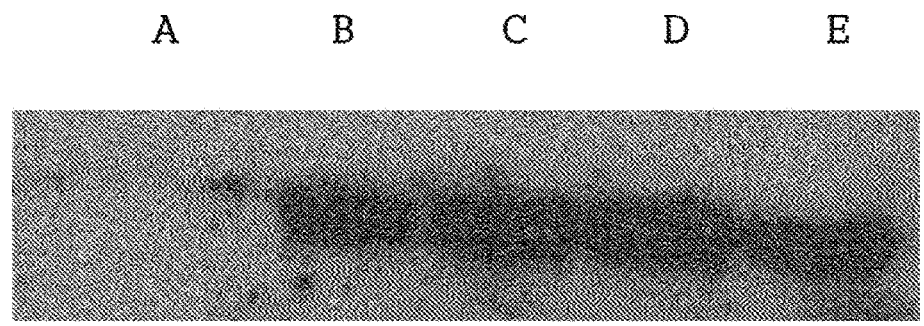
[Fig. 6]
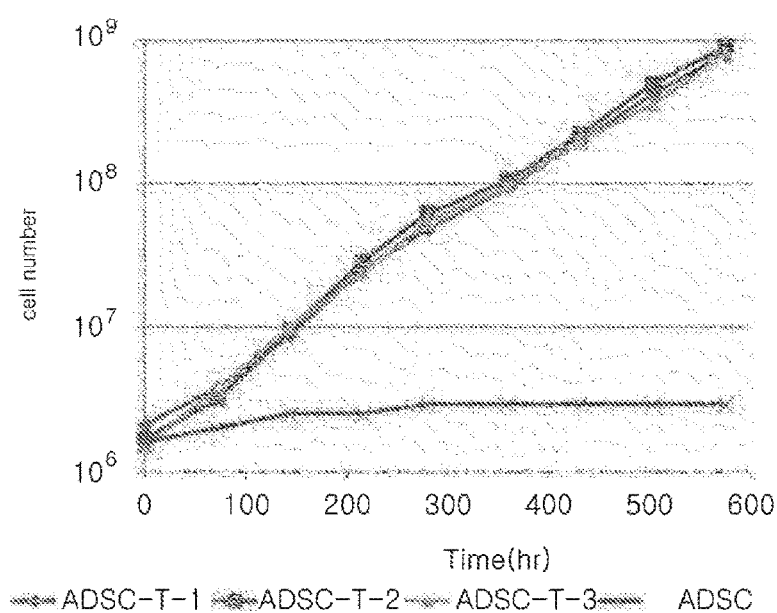

[Fig. 7]
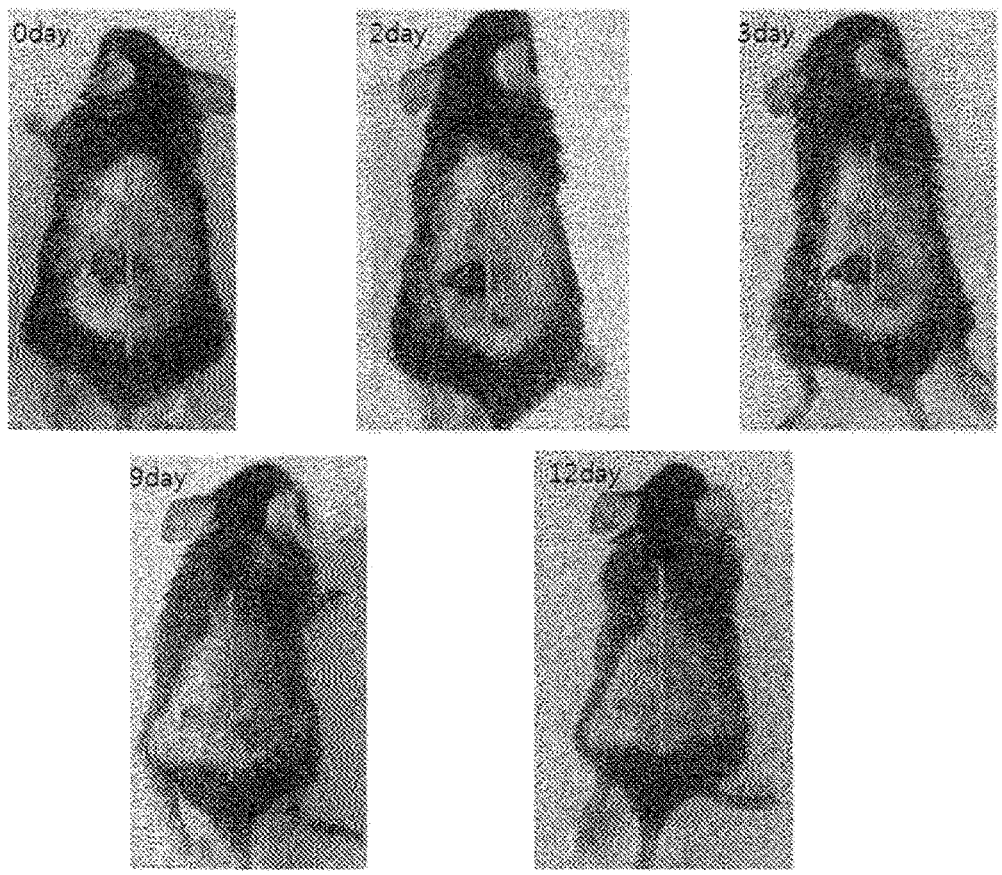
[Fig. 8]
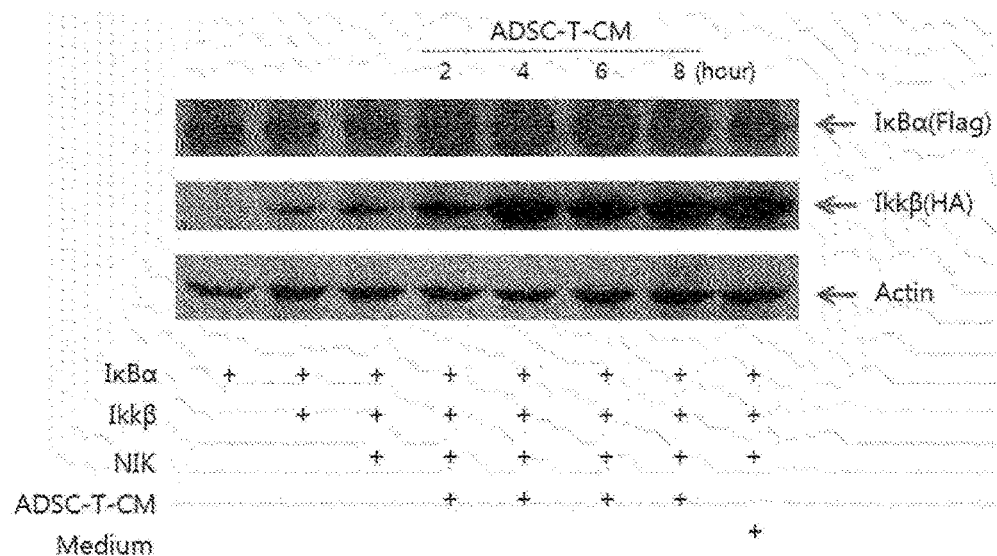

[Fig. 9]
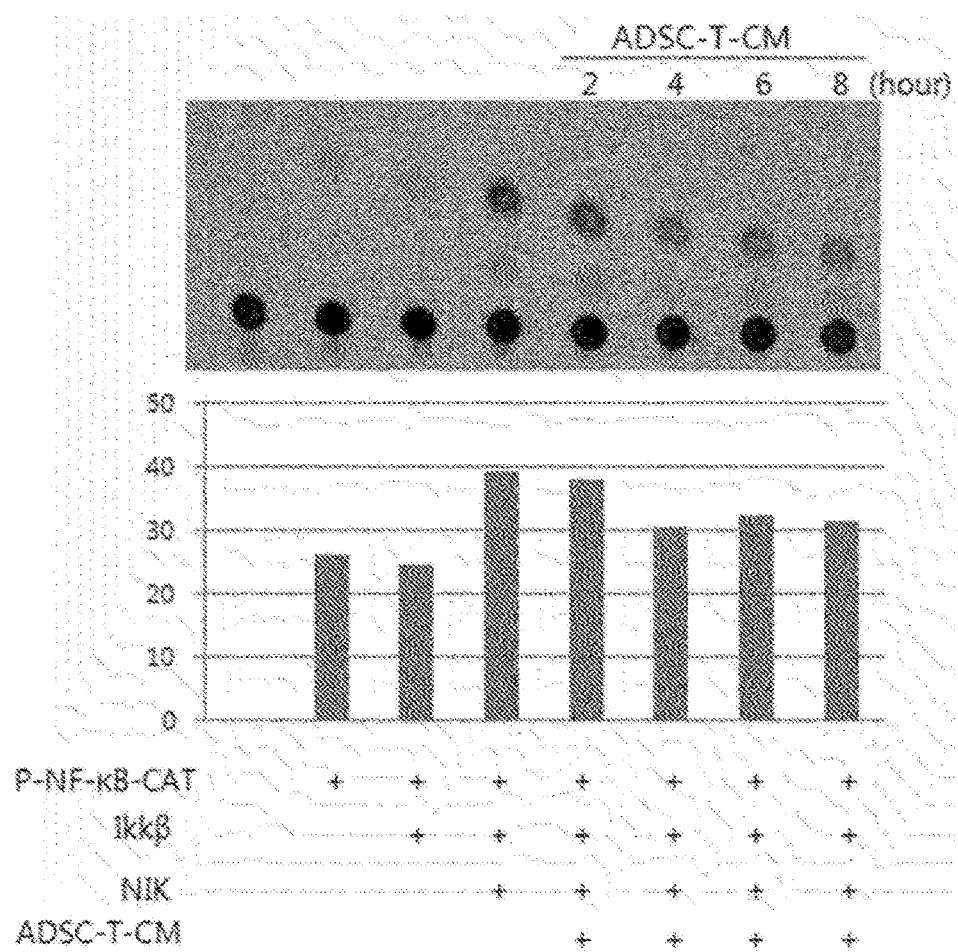

[Fig. 10]
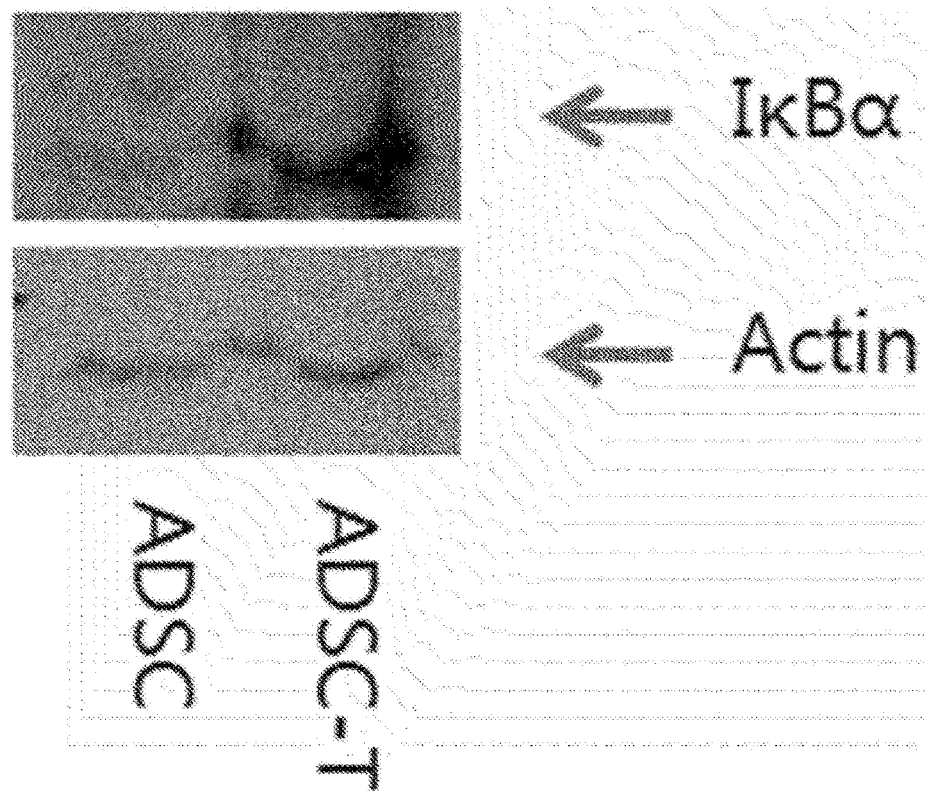
[Fig. 11]
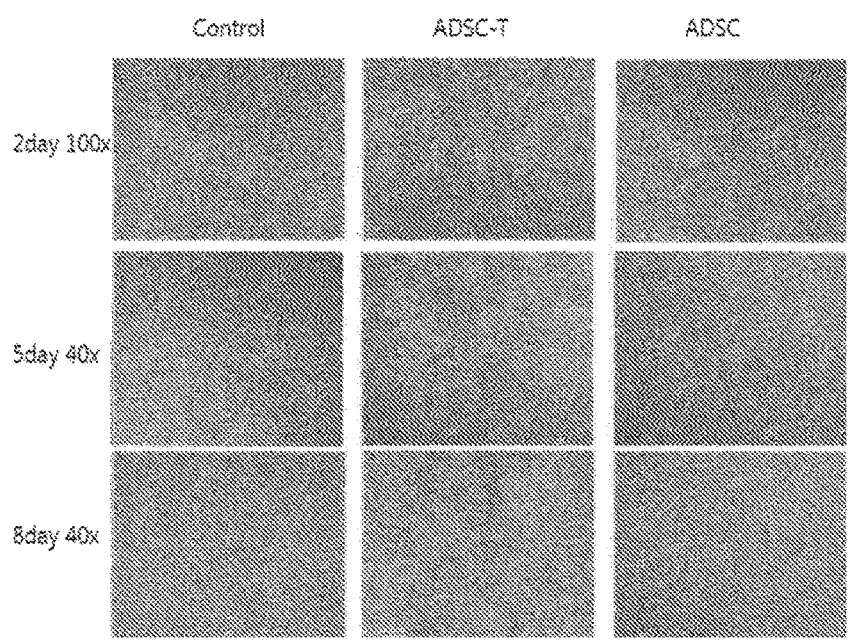

[Fig. 12]
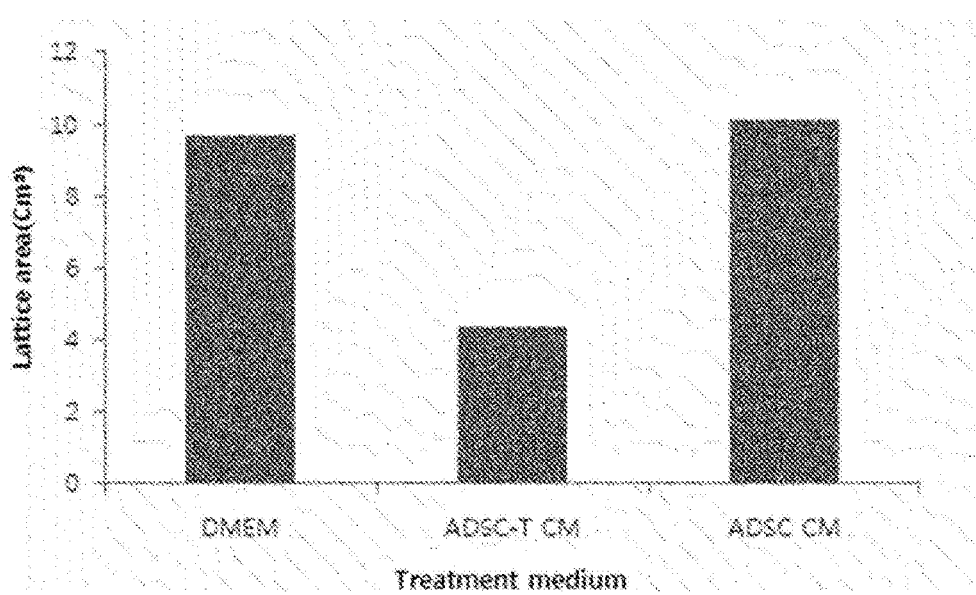
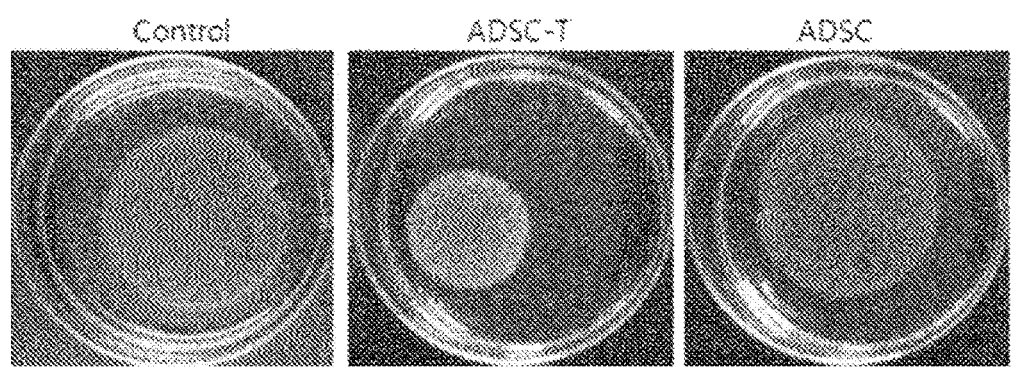

[Fig. 13]
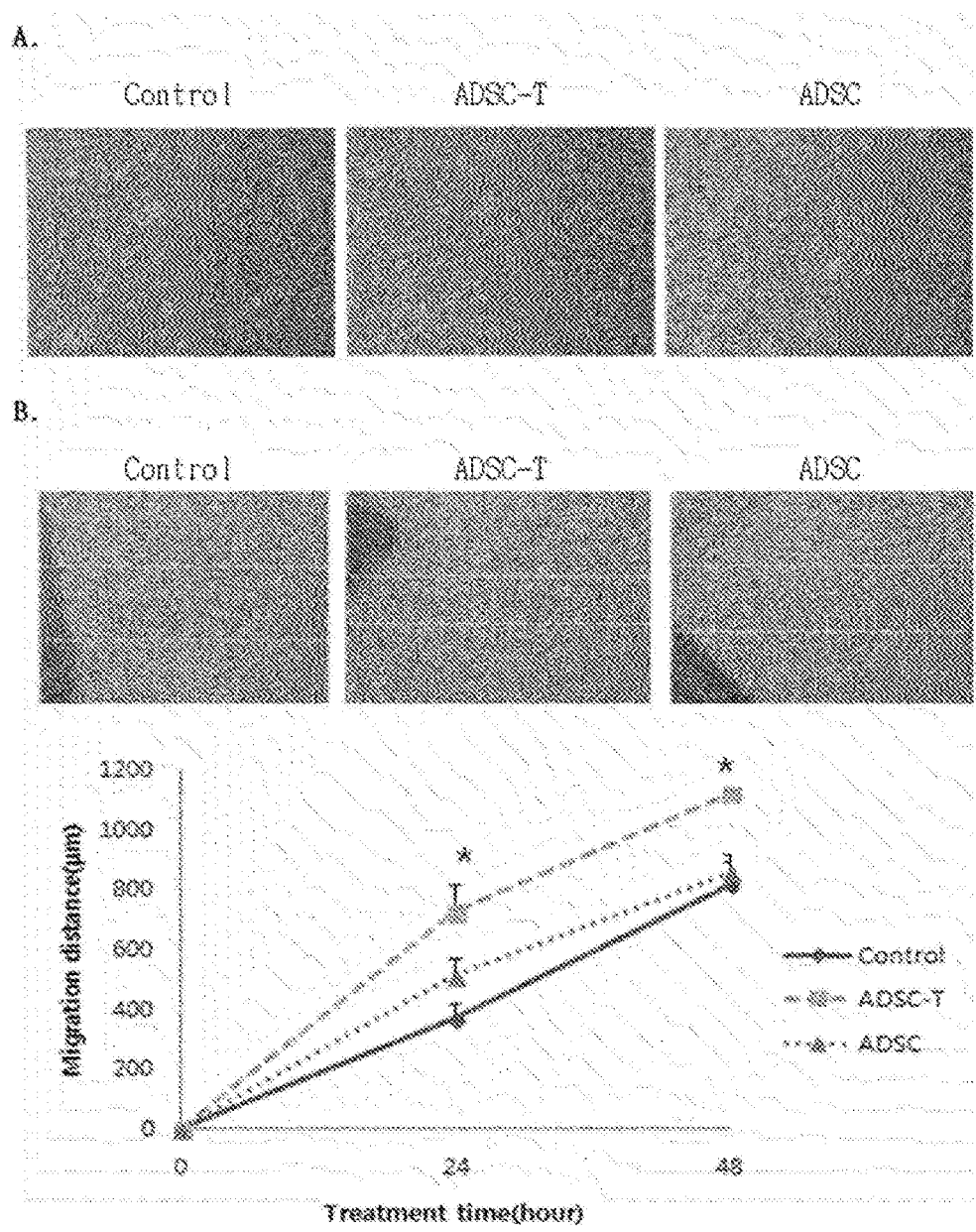

[Fig. 14]
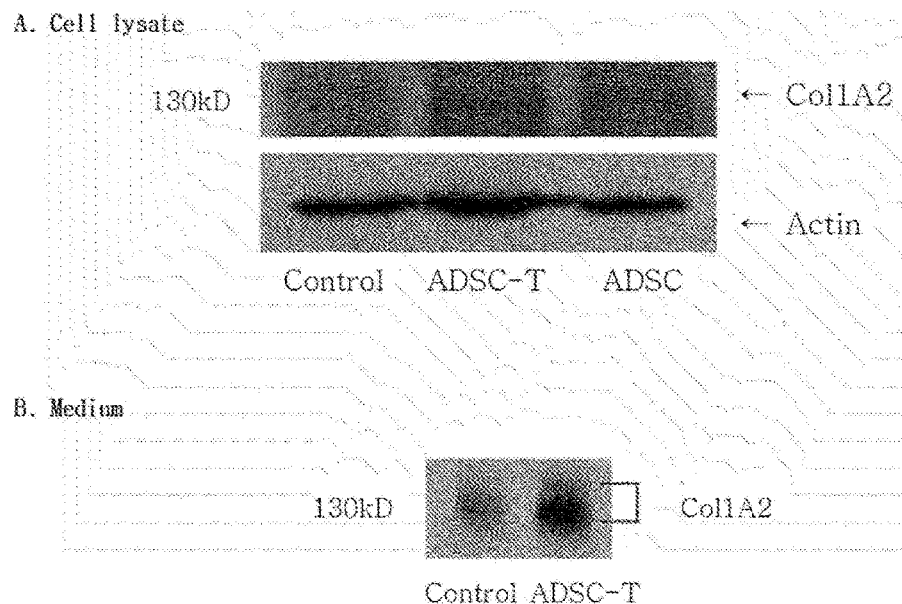
[Fig. 15]
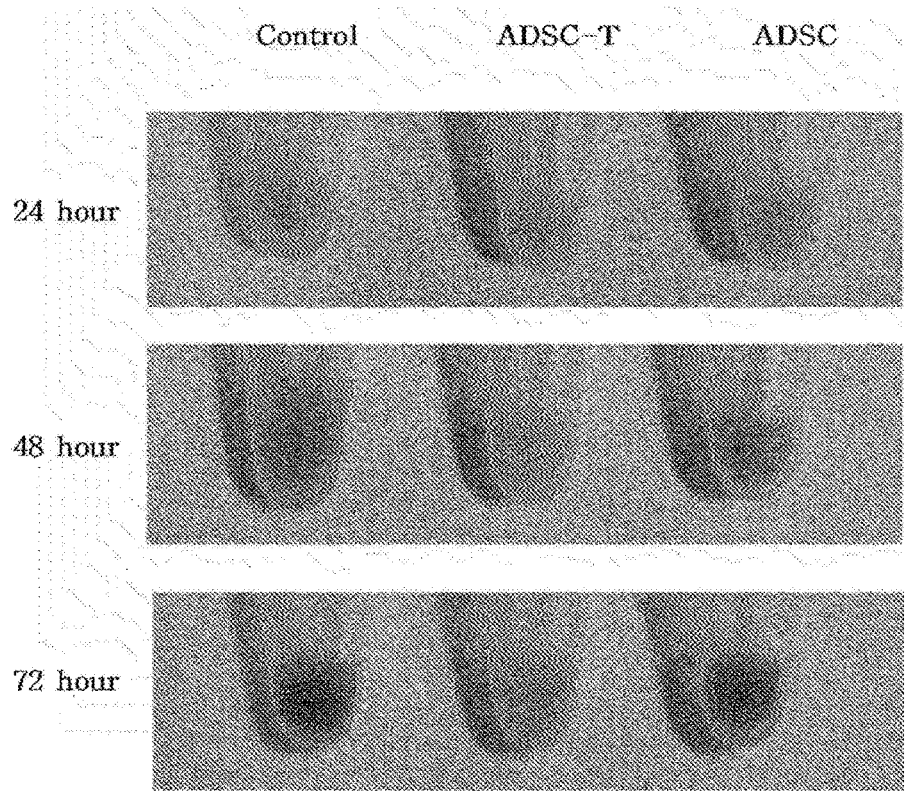

[Fig. 16]
A. Cell
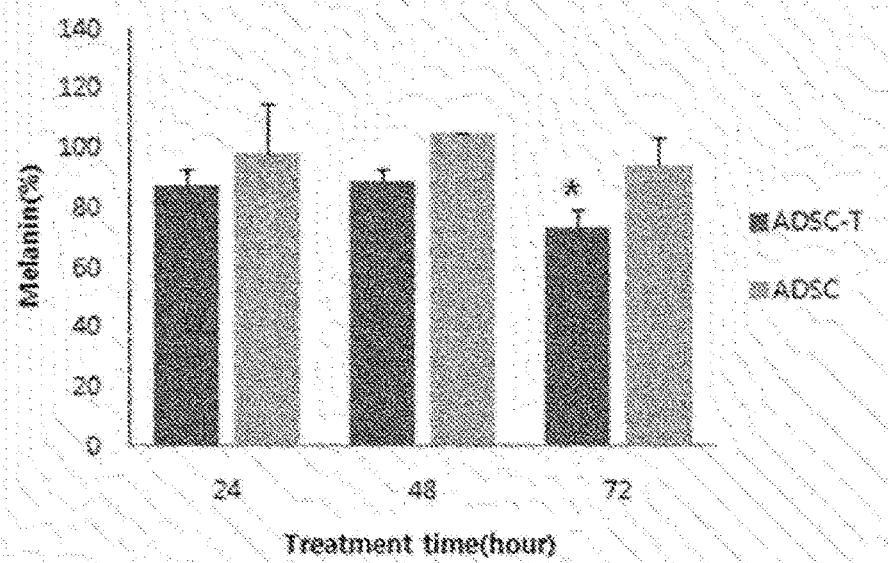
B. Medium
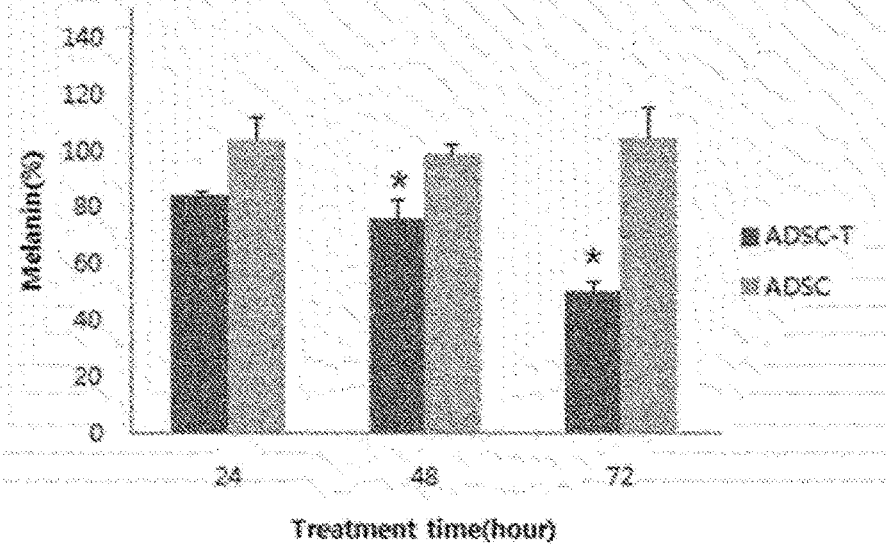

[Fig. 17]
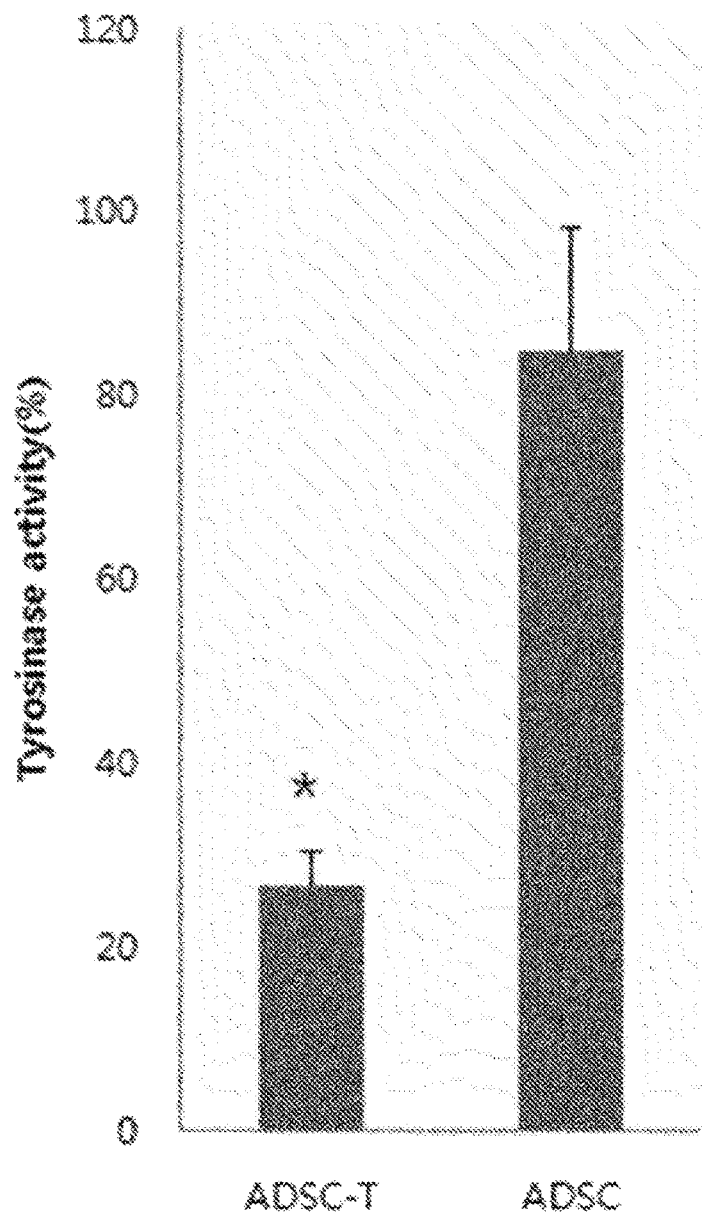

[Fig. 18]
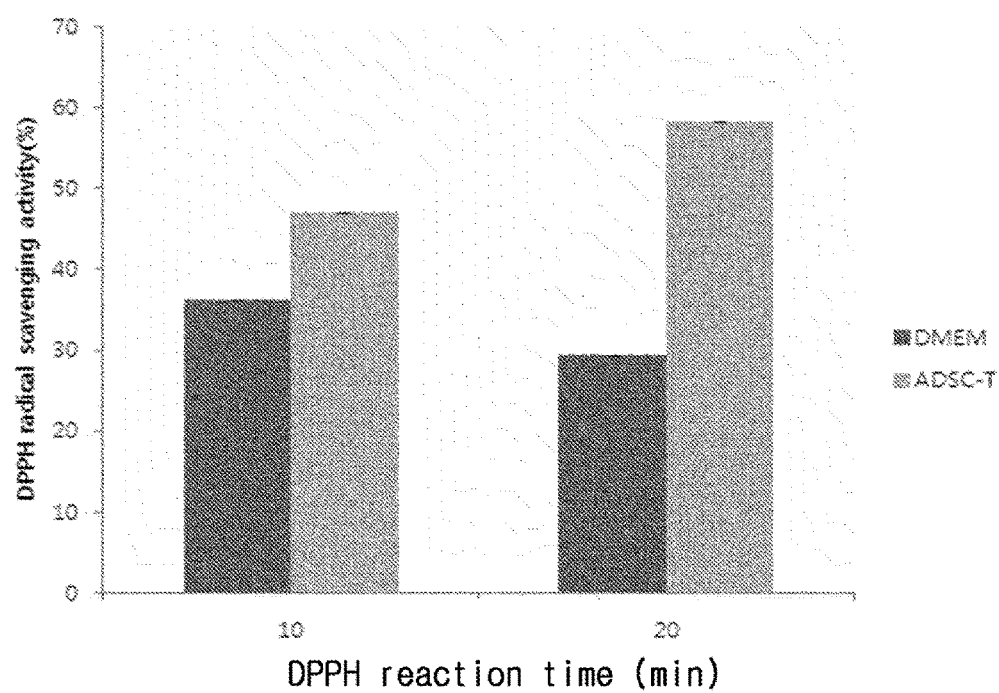

ant. Fibroblasts are involved in collagen production, and 90% of the dermis is composed of collagen. Collagen affects skin moisturizing and elasticity.

The regulation of inflammatory response is closely related to causes of inflammation-associated diseases, and the inflammatory response is associated with various signal transduction, for example, sequential activation of cyclooxygenase, NO synthetase, cytokine, etc. The excessive production of inflammatory mediators including NO, interleukin such as IL-6 and IL-1β, and TNF-α mediates inflammatory diseases, such as rheumatoid arthritis, inflammatory bowel diseases, osteoporosis, psoriasis, endotoxemia, toxic shock syndrome, etc. Inflammatory response occurring in human bodies can be broadly classified as acute inflammatory response and chronic inflammatory response. Acute inflammatory response is the response quickly occurring in order to protect the body from antigen introduced from the outside. The initialization of acute inflammation accompanies the secretion of inflammatory cytokines, such as interleukin-1 beta, interleukin-6, tumor necrosis factor-alpha (TNF-α), etc., and the increase of synthesis genes of inflammatory mediators, such as inducible nitric oxide synthase (iNOS), cyclooxygenase-2 (COX-2), etc. Macrophages activated by the secreted inflammation regulatory substances effectively remove introduced antigen, and once the antigen is completely removed, no further progress occurs. Thus, it is rare that acute inflammatory response leads to human diseases. However, in the case the acute inflammatory response develops into certain chronic inflammatory diseases, such as pertussis, the expression of IL-23 increases, and it develops into chronic inflammation (Infect. Immun., 73: 1590-1597, 2005). Unlike acute inflammatory response, chronic inflammatory response is the prolonged inflammatory response caused by internal causes in the body, rather than by external antigen, and results from in the increase of the expression of IL-17 and IL-23 due to inflammatory response including macrophages, neutrophils, and T lymphocytes, not simple inflammatory response by macrophages, and thereby the continuous expression of inflammatory cytokines such as TNF-α (Trends in Immunol, 27: 17-23, 2006) occurs. For the treatment of chronic inflammatory diseases, conventionally, the following drugs are most commonly used: anti-inflammatory drugs by steroids such as prednisolone, nonsteroidal anti-inflammatory drugs (NSAID) such as naproxen, and immunosuppressant drugs which combine with calcineurin such as cyclosporine or FK506, which is a calcium and calmodulin dependent protein phosphatase, to suppress the activity. However, these immunosuppressant drugs including steroids entail side effects, such as nephrotoxicity, inflammation, lymphoma, diabetes, tremor, headache, diarrhea, hypertension, nausea, renal dysfunction, etc. Thus, it is urgent to develop effective therapeutic agents for inflammatory diseases suppressing excessive expression of inflammatory mediators, while reducing side effects of the currently used therapeutic agents for inflammatory disease.

Further, the inflammatory response refers to a series of complex biological response such as secretion of inflammatory mediators activating enzymes, body fluid infiltration, cell migration, tissue damage, etc., which are associated with various inflammatory mediators and immune cells in topical blood vessels and body fluids when tissues (cells) are damaged or infected by external sources of inflammation (bacteria, viruses, fungi, various types of substances causing allergies), and external signs such as redness, swelling, heat, pain, etc. In normal cases, inflammatory response removes the external source of inflammation and regenerates dam-

ANTI-INFLAMMATORY, SKIN-REGENERATIVE, WHITENING, ANTIOXIDANT, OR WOUND-HEALING COMPOSITION CONTAINING CULTURE MEDIUM OF ADSC-T CELLS IN WHICH T-ANTIGEN IS INTRODUCED INTO ADIPOSE-DERIVED STEM CELL AS ACTIVE INGREDIENT

This application is the national stage of International Patent Application No. PCT/KR2013/007769, filed Aug. 29, 2013, which claims the benefit of Korean Patent Application No. 10-2013-0043527, filed Apr. 19, 2013, and Korean Patent Application No. 10-2013-0043536, filed Apr. 19, 2013.

TECHNICAL FIELD

The present invention relates to an anti-inflammatory, skin-regenerative, whitening, antioxidant, or wound-healing composition, including a culture medium of adipose-derived stem cell-T (ADSC-T) cells in which T-antigen is introduced into an adipose-derived stem cell as an active ingredient.

BACKGROUND ART

The average lifespan of human being approaches 100 by virtue of improvement of the 21$^{st}$ century medical development and the quality of life. As the lifespan of human being prolongs, people are more interested in preventing diseases and anti-aging. Wrinkles and freckles in the skin increase and skin-regeneration decrease due to external stimuli and body skin aging, as times go by. Through those signs, the body aging can be confirmed with eyes, and people are continuously and gradually interested in preventing the skin aging and use therapeutic agents and cosmetics for preventing a variety of skin aging. To meet the interests, cosmetic companies continuously search for novel substances.

For existing whitening and anti-aging effective substances, arbutin, ascorbic acid derivatives selina, etc., are used.

Skin pigmentation occurs in association with the production of melanin in melanocytes. The production of melanin increases due to external stimuli (UV, inflammation) and active oxygen in the body. The melanin production pathway is as follows: tyrosine is oxidized to dopa, then to dopaquinone, and becomes 5,6-dihydroxyindole-2-carboxylic acid by dopachrome, and then a final eumelanin is produced. Tyrosinase, which is involved in the pathway of the oxidation of tyrosine to dopaquinone and the formation of 5,6-dihydroxyindole-2-carboxylic acid, is the most important enzyme for the production of melanin. Thus, the inhibition of tyrosinase is a main target in searching for substances with whitening effects.

Anti-aging associated substances include retinoid, silicic acid, mevalonolactone (mevalonic acid, MA), adenosine, retinyl palmitate, etc. They have effects of regulating skin cell regeneration, collagen production regulation, wrinkle improvement, etc. In order to prevent skin aging, the activation of skin cell regeneration, promotion of collagen formation, antioxidant activity, etc., are necessary. The skin is composed of the epidermis, dermis, and subcutaneous tissue, and fibroblast in the dermis significantly affects skin aging. Cellular aging resulting from the reduction of the number of fibroblasts causes the damage on skin tissues.

Also, in skin wound repair processes, the migration and proliferation of fibroblasts and wound contraction are imporaged tissues, so as to repair the functions of living things. However, if antigen is not removed or inflammatory response excessively or continuously occurs because of internal substances, damage on mucous membranes is promoted, which leads to some diseases, such as cancer. As causes of inflammation production in the body, various biochemical phenomena are involved in inflammation, and particularly, it is known that nitric oxide synthase (NOS) generating nitric oxide (NO) and enzymes associated with biosynthesis of prostaglandin play an important role in mediating inflammatory response. Thus, NOS generating NO from L-arginin or cyclooxygenase (COX) associated with synthesis of prostaglandins from arachidonic acid are main targets for blocking inflammation. According to previous studies, NO generated in a small amount by NOS which is expressed at a constant level in blood vessels and nerves plays an important role in maintaining homeostasis of normal bodies which induces neurotransmission and vasodilation. However, NO generated by induced NOS (iNOS) which is induced by various cytokines or external stimuli is known to cause cytotoxic or various inflammatory responses, and chronic inflammation is associated with the increase of iNOS activity (Appleton L. et al Adv. Phamacol., 35. 27-28. 1996).

According to another studies, cyclooxygenase includes two types of isoforms, of which cyclooxygenase-1 (COX-1) always resides in cells and synthesizes prostaglandins (PGs) necessary for cell protection, and COX-2 rapidly increases in cells in the inflammatory response and is known as playing a significant role in the inflammatory response.

Up to now, for anti-inflammatory drugs used for alleviating inflammation, nonsteroidal anti-inflammatory drugs include ibuprofen, flufenamic acid, indomethacin, etc., and steroidal anti-inflammatory drugs include prednisolone, dexamethasone, etc. Allantoin, glycyrrhetinic acid, and derivatives thereof are known to have anti-inflammatory effects. However, the development of raw materials having anti-inflammatory effects enough for consumers to feel the effects is still required.

Meanwhile, stem cells refer to cells having the potency to be differentiated into all types of cells constituting the body, such as nerves, blood, cartilage, etc., when required, while maintaining to be undifferentiated into specific cells. There are broadly two methods for obtaining these stem cells: first, obtaining from embryos generated from fertilized eggs (embryonic stem cells), and second, recollecting stem cells maintained in every part of the body in adults (adult stem cells). Embryonic stem cells and adult stem cells, although differ from each other in terms of functions, have the potency to be differentiated into various types of cells. Embryonic stem cells have excellent differentiating potency and long telomers, while having disadvantages of raising ethnical issues and having difficulty in obtaining a large amount of cells. In comparison, adult stem cells may obtain a large number of cells, while having disadvantages of posing risk of inflammation when transplanted into another body or having relatively low differentiating potency.

Despite the above disadvantages, adult stem cells are greatly stable for medical applications. Also, adipose-derived stem cell (ADSC), which can be readily obtained from suctioned lipid, does not raise ethical issues and can be readily obtained.

The primary ADSC is highly commercially applicable, but is not suitable for mass production of the culture media of stem cells due to slow growth rate and short lifespan.

In order to overcome the disadvantage, the present inventors prepared ADSC-T cell line in which T antigen of simian virus (SV 40) is introduced. The cell line has a threefold increase in proliferation rate and about 6-month prolonged cell lifespan, compared with primary ADSC line. Thus, the present invention supplements the disadvantage the primary ADSC line has with regard to mass production of culture media through the production of ADSC-T cell line in which T antigen is introduced into ADSC.

As a result of studies conducted by the present inventors to solve the issues on treatment, prevention, or improvement of anti-inflammation, skin-regeneration, whitening, antioxidant activity, or wound-healing, the present inventors established ADSC-T cell line in which T antigen is introduced into ADSC, and confirmed anti-inflammatory, skin-regenerative, whitening, antioxidant, or wound-healing effects of culture media of ADSC-T cell, and thereby completed the present invention.

SUMMARY OF INVENTION

It is an object of the present invention to provide a pharmaceutical composition for preventing or treating inflammatory diseases, including a culture medium of adipose-derived stem cell-T (ADSC-T) cells in which T-antigen is introduced into an adipose-derived stem cell as an active ingredient.

It is another object of the present invention to provide a food composition for preventing or improving inflammatory diseases, including a culture medium of ADSC-T cells in which T-antigen is introduced into an adipose-derived stem cell as an active ingredient.

It is yet another object of the present invention to provide a cosmetic composition for skin-regeneration, whitening or anti-oxidation, including a culture medium of ADSC-T cells in which T-antigen is introduced into an adipose-derived stem cell as an active ingredient.

It is yet another object of the present invention to provide a food composition for skin-regeneration, whitening or anti-oxidation, including a culture medium of ADSC-T cells in which T-antigen is introduced into an adipose-derived stem cell as an active ingredient.

It is yet another object of the present invention to provide a pharmaceutical composition for wound-healing, including a culture medium of ADSC-T cells in which T-antigen is introduced into an adipose-derived stem cell as an active ingredient.

In order to achieve the above objects, the present invention provides a pharmaceutical composition for preventing or treating inflammatory diseases, including a culture medium of adipose-derived stem cell-T (ADSC-T) cells in which T-antigen is introduced into an adipose-derived stem cell as an active ingredient.

Also, the present invention provides a food composition for preventing or improving inflammatory diseases, including a culture medium of ADSC-T cells in which T-antigen is introduced into an adipose-derived stem cell as an active ingredient.

Also, the present invention provides a cosmetic composition for skin-regeneration, whitening or anti-oxidation, including a culture medium of ADSC-T cells in which T-antigen is introduced into an adipose-derived stem cell as an active ingredient.

Also, the present invention provides a food composition for skin-regeneration, whitening or anti-oxidation, including a culture medium of ADSC-T cells in which T-antigen is introduced into an adipose-derived stem cell as an active ingredient.

Also, the present invention provides a pharmaceutical composition for wound-healing, including a culture medium of ADSC-T cells in which T-antigen is introduced into an adipose-derived stem cell as an active ingredient.

The culture medium of ADSC-T cell lines, according to the present invention, has remarkable effects for treating or inhibiting inflammation by alleviating atopic dermatitis, which is an autoimmune disease, and inhibiting NF-κB activities through an increase of an Iκbα expression. Additionally, the culture medium, according to the present invention, exhibits excellent skin regenerative effects by having effects of enhancing skin collagen elasticity and reducing wounds in a collagen culture, excellent skin whitening effects by inhibiting tyrosinase activities and melanin production, and excellent anti-oxidation effects by inhibiting DPPH radical activities. Furthermore, the present invention has remarkable wound-healing effects by enhancing cell mobility of fibroblast, and is thus useful for anti-inflammation, skin-regeneration, whitening, anti-oxidation, or healing wounds.

BRIEF DESCRIPTION OF THE DRAWINGS

FIG. 1A is a view illustrating all cells isolated from suctioned adipose tissues observed with a microscope after smearing the cells on plates, and FIG. 1B is a view illustrating the cells attached on the plates subjected to passage after the floating cells are removed (×100 magnification, respectively).

FIG. 2 is a view illustrating a result of staining the cells with Oil-Red O, in order to confirm whether adipose-derived stem cells (ADSC) are differentiated into adipocytes [(A) before induction of differentiation of ADSC, (B) 30 days after induction of differentiation, and (C) a result of staining the cells with Oil-Red O 30 days after induction of differentiation].

FIG. 3 is a view illustrating the morphological changes of ADSC-T cells with a microscope [(A) primary ADSC, (B, C) high-density focus of ADSC formed by introducing pEF321 β-T plasmid, and (D) ADSC-T cells established by culturing cells obtained from the high-density focus] (×100 magnification, respectively).

FIG. 4 is a view illustrating SV40 T antigen expressed in ADSC-T and COS-1 cells which is used as a control group, observed by a fluorescent antibody staining method.

FIG. 5 is a view illustrating a result of a Western blotting analysis of T antigen of ADSC-T cells using a monoclonal antibody of T antigen [(A) primary ADSC, (B, C, D) ADSC-T, and (E) COS-1].

FIG. 6 is a view illustrating the proliferation rates of the primary ADSC and three cells (ADSC-T-1, ADSC-T-2, and ADSC-T-3) of ADSC-T.

FIG. 7 is a view illustrating the effect of the culture medium of ADSC-T cells of the present invention in which T antigen is introduced into ADSC on atopic dermatitis.

FIG. 8 is a view illustrating the effect of the culture medium of ADSC-T cells of the present invention in which T antigen is introduced into ADSC on decomposition of IκBα.

FIG. 9 is a view illustrating the effect of the culture medium of ADSC-T cells of the present invention in which T antigen is introduced into ADSC on inhibition of NF-κB.

FIG. 10 is a view illustrating the expression level of IκBα in ADSC and ADSC-T cells of the present invention in which T antigen is introduced into ADSC.

FIG. 11 is a view illustrating the morphology of 3Y1 cells in collagen gel. 3Y1 cells were cultured on collagen gel in media containing 50% culture medium of ADSC-T or ADSC, for the respectively indicated time periods.

FIG. 12 is a view illustrating the contraction effect of the culture medium of ADSC-T on a fibroblast-populated collagen lattice (FPCL) model. 3Y1 cells were cultured on collagen gel for 8 days using 50% culture medium of ADSC-T or ADSC, and then the square of collagen was calculated.

FIG. 13 is a view illustrating the effect of the culture media of ADSC-T and ADSC on fibroblast mobility. A shows the mobility of 3Y1 cells at 48 hours after treatment with each of the culture medium, and B is a graph showing cell migration distances according to the time (value=average±standard deviation, n=0.3) [*P<0.05].

FIG. 14 is a view illustrating the production of collagen by 3Y1 cells after treatment with the culture medium. The cells were cultured for 5 days using 50% culture media of ADSC-T, ADSC and 3Y1 cells. The lysate and culture medium of 3Y1 cells were used for a western blotting of collagen type I.

FIG. 15 is a view illustrating cell pellets of B16F10 after treatment with the culture medium of ADSC-T or ADSC. The cells were cultured for the respectively indicated time periods and obtained, and then centrifuged cell pellets were shown with photographs taken by a digital camera.

FIG. 16 is a view illustrating the effects of the culture medium of ADSC-T or ADSC regarding the amount of melanin in B16F10 cells. The amounts of melanin in cells (A) and media (B) were measured at 492 nm with a spectrophotometer (value=average±standard deviation, n=3) [*P<0.05].

FIG. 17 is a view illustrating the effects of culture media of ADSC-T and ADSC on tyrosinase activity in B16F10 cells. B16F10 cells were cultured using a media containing 50% culture media of ADSC-T and ADSC, and the tyrosinase activity was measured with a lysate after 48 hours (value=average±standard deviation, n=3) [*P<0.05].

FIG. 18 is a view illustrating DPPH free radical scavenging activity the culture medium of ADSC-T. The culture medium of ADSC-T and 0.13 mM DPPH in the same volume were mixed and reacted for the respectively indicated time periods, and the free radical scavenging activity was measured at OD 515 nm (value=average±standard deviation, n=3) [*P<0.05].

BEST MODE FOR CARRYING OUT THE INVENTION

The present invention relates to an anti-inflammatory, skin-regenerative, whitening, antioxidant, or wound-healing composition, including a culture medium of adipose-derived stem cell-T (ADSC-T) cells in which T-antigen gene of Simian virus (SV40) is introduced into an adipose-derived stem cell as an active ingredient.

The composition includes a pharmaceutical composition, a food composition or a cosmetic composition.

Hereinafter, the present invention will be described in more detail.

The present inventors expected that on the basis that the lifespan of various cells was extended by the expression of a T antigen of SV40, the lifespan of the adipose-derived stem cell could be extended by isolating stem cells from suctioned adipose (adipose-derived stem cells, ADSC), and then introducing the vector expressing a T antigen of SV40 in order to increase the proliferation rate of the isolated adipose-derived stem cells and extend the proliferation lifespan. In order to identify the above content, pEF321β-T plasmid that is a vector expressing a T antigen of SV40 is introduced into an adipose-derived stem cell. As a result, it may be confirmed that the lifespan of the adipose-derived stem cell expressing a T antigen of SV40 is extended and the proliferation rate thereof is improved.

In the present invention, "Simian Virus 40 (SV40)," a virus that belongs to a polyoma virus family, a polyoma virus genus, and simian virus 40 species, has a circular double-strand dielectric formed of 5245 bases, has a wide host range, and thus, is used as a transformation vector of a cell.

The "T antigen" of SV40 is an early protein that is synthesized at the beginning of the infection of SV40 that is a virus leading to a tumor, and is a protein contributing to the canceration of the infected cell. The T antigen has a function of suppressing the activity of a tumor inhibitory gene product (p53, and the like) by binding with the tumor inhibitory gene product (p53, and the like) of the cell during the transformation of the cells, and thus, is applied to the immortalization of various cells.

The culture medium of an adipose-derived stem cell (ADSC-T), which is an active ingredient of the composition of the present invention may be prepared by (a) culturing the adipose-derived stem cell after isolating the adipose-derived stem cell through a centrifuge after treating an enzyme, collagenase, to a suctioned adipose tissue, (b) preparing an adipose-derived stem cell (ADSC-T) expressing a T antigen of SV40 by transfecting a plasmid expression vector (pEF321β-T) into the adipose-derived stem cell cultured from the above step (a), and (c) obtaining a culture medium by culturing the adipose-derived stem cell (ADSC-T) prepared in the above step (b).

The method for preparing a culture medium of an adipose-derived stem cell according to the present invention will be described in detail in sequence as follows:

The above step (a) is a step for culturing an adipose-derived stem cell isolated from a suctioned adipose tissue, in which first, an enzyme, collagenase, is mixed with the suctioned adipose tissue in a weight ratio of 1:1, treated at 30 to 40° C. for 40 to 50 minutes, and then centrifuged to isolate the adipose-derived stem cell.

The above enzyme "collagenase" is an enzyme promoting the hydrolysis of collagen, and plays a role in isolating each of the adipose stem cells by decomposing the collagen of an adipose tissue. The centrifugation may be carried out at 500 to 1000 G for 2 to 5 minutes, and preferably, at 800 G for 3 minutes. After the lipid and adipocyte layer that are floated on the supernatant are removed, cellular residue is removed using a filter. The filter is preferably a 100 μm filter, but it is not limited thereto.

After removing the cellular residue, normal saline solution is added thereto, and then the centrifugation is repeated to clean the cell. The centrifugation may be carried out at 150 to 500 G for 2 to 5 minutes, and preferably, may be carried out at 300 G for 3 minutes.

The isolated adipose-derived stem cell (ADSC) is cultured in Dulbecco's Modified Eagle Media (DMEM) added with 10% Fetal Bovine Serum (FBS), 100 units/ml of penicillin, and 100 μg/ml of streptomycin in an incubator of 37° C. and 5% $CO_2$. When the confluence of the cells reaches 80 to 90%, the sub-culture is carried out. As the above culture method, the cell culture method that is known in the art may be applied.

The above step (b) is a step for preparing an adipose-derived stem cell (ADSC-T) expressing a T antigen of SV40, in which a plasmid expression vector (pEF321β-T) is transfected into the adipose-derived stem cell isolated in the above step (a) to obtain the adipose-derived stem cell (ADSC-T) expressing a T antigen of SV40.

The "vector" is DNA capable for a desired DNA fragment to be introduced into a host cell for a DNA recombination experiment, and the vector DNA is cleaved and opened by restriction enzymes, and then connected by inserting a desired DNA fragment, thereby introducing the desired DNA fragment into a host cell. The vector DNA connecting the desired DNA fragment is inserted into chromosome DNA of the host cell, and thus, distributed to each of the cells according to the host cell division. Therefore, the desired DNA fragment is maintained, and thus, is connected from generation to generation.

The plasmid expression vector means the plasmid including nucleic acid sequences encoding a T antigen of SV40, and preferably pEF321β-T is used.

The "transfection" means to cause a gene introduction and infection by injecting gene DNA, plasmid DNA, virus DNA. RNA, and the like through the culture medium of cells or suspension of cells into a cell. In detail, the transfection of the expression vector may be carried out by using all of the available transfection methods including a calcium phosphate transfection, an electroporation, a microinjection, a liposome injection, and the like, which are known in the art. In addition, DNA may be introduced into eukaryotic cells using virus or bacteria as a carrier.

For example, a method of introducing the pEF321β-T plasmid using the electroporation may be carried out by using a method including mixing an adipose-derived stem cell with a plasmid in a nonserum culture medium, preferably, a nonserum DMEM, and then performing an electric shock, but the present invention is not limited thereto. In addition, the plasmid may be introduced by using the electroporation protocol that is known in the art.

For the cell introduced with a foreign gene, the expression of the gene introduced by the culture for a certain time is induced, and then whether or not the expression thereof is induced should be verified. The culture for expressing the introduced gene is preferably carried out in 5% $CO_2$ incubator at 37° C., but the present invention is not limited thereto. The gene introduced for the present invention is a gene expressing a T antigen of SV40, and whether or not the expression of T antigen is carried out may be verified by detecting the T antigen expressed in an adipose-derived stem cell through an antigen-antibody binding reaction using an antigen that is specifically bound to the T antigen. In detail, it may be verified by using a general enzyme immunoassay (ELISA), a radioimmunoassay (RIA), a sandwich assay, an immunochitochemical staining, an antigen-antigen aggregation assay, and the like. Also, whether or not the expression of T antigen is carried out may be verified with a western blot assay and fluorescent antibody staining assay.

The above step (c) is a step for obtaining a culture medium by culturing an adipose-derived stem cell (ADSC-T) manufactured in the step (b) above, in which the culture medium is obtained by culturing ADSC-T cells in $1 \times 10^5$ cell/ml, sub-culturing the cells after the cell confluence reaches 80%, and collecting the culture medium 2 days after the cell confluence reaches 70 to 90%.

The above-obtained culture medium is centrifuged to remove cell residue and collect only a supernatant. The centrifugation is carried out at 500 to 1000 G for 2 to 5 minutes, and preferably, at 800 G for 3 minutes.

As the culture medium of ADSC-T cells, a basal medium known in the art may be used without limitation. The basal medium may be prepared by being manually synthesized, or a commercially available medium may be used. Examples of the commercially available medium include Dulbecco's Modified Eagle's Medium (DMEM), Minimal Essential Medium (MEM), Basal Medium Eagle (BME), RPMI 1640, F-10, F-12, α-Minimal essential Medium (α-MEM), Glasgow's Minimal Essential Medium (G-MEM) and Iscove's Modified Dulbecco's Medium, but are not limited thereto. Also, the cell culturing medium may contain one or more supplements, which includes at least one selected from the group consisting of antibiotics such as Penicillin G, streptomycin sulfate, and gentamycin to prevent microbial contamination, anti fungal agents such as amphotericin B and nystatin, and mixtures thereof, in addition to serum from calf/horse/human.

The culture medium of ADSC-T cells, according to the present invention, has remarkable effects for treating or inhibiting inflammation by alleviating atopic dermatitis, which is an autoimmune disease, and inhibiting NF-κB activities through an increase of an IκBα expression. Additionally, the culture medium, according to the present invention, exhibits excellent skin regenerative effects by having effects of enhancing skin collagen elasticity and reducing wounds in a collagen culture, excellent skin whitening effects by inhibiting tyrosinase activities and melanin production, and excellent anti-oxidation effects by inhibiting DPPH radical activities. Furthermore, the present invention has remarkable wound-healing effects by enhancing cell mobility of fibroblast, and is thus useful for anti-inflammation, skin-regeneration, whitening, anti-oxidation, or healing wounds.

In the present invention, "inflammatory disease" means chronic or acute inflammatory diseases. Chronic inflammation is considered to be inflammation of a prolonged duration (week or months) in which active inflammation, tissue destruction and attempts for healing are proceeding simultaneously (Robbins Pathological Basis of Disease by R. S. Cotran, V. Kumar, and S. L. Robbins, W. B. Saunders Co., p. 75, 1989. Although chronic inflammation may follow an acute inflammatory episode, it may also begin as an insidious process that proceeds with time, for example, as a result of a persistent infection (e.g., tuberculosis, syphilis, fungal infection) that causes a delayed hypersensitivity reaction, prolonged exposure to endogenous (e.g., elevated plasma lipids) or exogenous (e.g., silica, asbestos, cigarette tar, surgical sutures) toxins, or autoimmune reactions against the body's own tissues (e.g., rheumatoid arthritis, systemic lupus erythematosus, multiple sclerosis, psoriasis). Thus, chronic inflammation may include various medical conditions such as rheumatoid arthritis, restenosis, psoriasis, multiple sclerosis, post-surgical adhesion, tuberculosis, and chronic inflammatory lung diseases (e.g., asthma, pneumoconiosis, chronic obstructive pulmonary diseases, nasal polyp and pulmonary fibrosis). More specifically, the inflammatory diseases mean at least one selected from allergic disease, atopic dermatitis, nasitis, asthma, acute pain, chronic pain, paradentitis, gingivitis, inflammatory bowel disease, gout, myocardial infarction, arteriosclerosis, congestive heart failure, hypertension, angina pectoris, stomach ulcer, Alzheimer's disease, cerebral infarction, Down's syndrome, multiple sclerosis, obesity, diabetes, dementia, depression, schizophrenia, tuberculosis, sleep disorder, sepsis, a burn, and pancreatitis.

The pharmaceutical composition of the present invention may include a pharmaceutically acceptable carrier, and may be formulated into a transdermal dosage such as liquid, suspension, emulsion, lotion, ointment, etc. according to a known method. The pharmaceutically acceptable carrier may include aqueous diluents or solvents such as phosphate buffered saline, purified water, sterile water, etc., and non-aqueous diluents or solvents such as propylene glycol, olive oil, etc. Also, it may optionally include a wetting agent, flavoring agent, preservative, etc. The culture medium of adipose-derived stem cell-T (ADSC-T) cells contained in the pharmaceutical composition may vary depending on the patient's state and weight, the severity of disease, the form of drug, and administration route and duration, but may be appropriately selected by those skilled in the art. For example, the culture medium of adipose-derived stem cell may be administered at a dose of 0.01 to 100 mg/kg per day, and preferably at a dose of 0.1 to 10 mg/kg per day. The daily dose may be administered once a day or in equally divided doses.

The carrier(s) should not be harmful to receptors, and should be "acceptable" in terms of compatibility with other ingredients of the formulation. In light of the above, a pharmaceutically acceptable carrier intends to include any and all solvents, dispersion media, coatings, antibacterial and antifungal active agents, isotonic and absorption delaying agents, etc. The use of such media and active agents for pharmaceutical active substances is well known in the art. Except insofar as any conventional media or active agent is incompatible with the active compound, its use in the therapeutic compositions is contemplated. Supplementary active compounds (those known in the pertinent art and/or suggested or designed according to the present invention) may also be incorporated into the compositions. The formulation may conveniently be presented in unit dosage form and may be prepared by any methods well known in the art of pharmaceutical/microbiology. In general, the formulations are prepared by bringing into association the compound with liquid carriers or finely divided solid carriers or both, and then if necessary shaping the product into a suitable formulation.

The pharmaceutical composition of the present invention may be formulated to be suitable for a desired administration route. The administration route may be oral, ocular and nasal, or may include parenteral routes such as intravenous, intramuscular, subcutaneous, transdermal, transmucosal, and rectal administration. The solution or suspension used for parenteral administration or intramuscular or subdermal application may include the following ingredients: sterile diluents such as water for injection, salt water, fixed oil, polyethylene glycol, glycerin, propylene glycol or other synthetic solutions; anti-bacterial agents such as benzyl alcohol or methyl parabene; antioxidants such as ascorbic acid or sodium bisulfite; chelating agents such as ethylenediaminetetraacetic acid; buffers such as acetate, citrate or phosphate; and tension controllers such as sodium chloride or dextrose. The pH may be acid or alkali, for example, controlled with hydrochloric acid or sodium hydroxide.

The solution useful for oral or parenteral administration may be prepared by any of the methods well known in the pharmaceutical art, for example as described in Remington's Pharmaceutical Sciences [(Gennaro, A., ed.), Mack Pub., (1990)]. The formulation for parenteral administration may also include glycocholates for oral administration, methoxy salicylate for rectal administration, or citric acid for vaginal administration. Parenteral formulations may be enclosed in ampoules, disposable syringes or multi-capacity vials made of glass or plastic. Suppositories for rectal administration may also be prepared by mixing the drug with a non-irritating excipient such as cocoa butter or other glyceride, or another composition which is solid at room temperature and liquid at body temperature. The formulation may include, for example, polyalkylene glycol such as polyethylene glycol, oil of plant origin, or hydrogenated naphthalene. The formulation for direct administration may contain glycerol and other highly viscous compositions. Other potentially useful parenteral carriers for these preparations include particles of ethylene-vinyl cerotate copolymer, osmotic pump, portable implant, and liposomes. Preparations for inhale administration may include an excipient such as lactose and/or an aqueous solution containing polyethylene oxide-9-lauryl ether, glycocholate and deoxycholate, an oil solution as nasal drops, or a gel for intranasal administration. For rectal delivery, retention enema may be used.

The formulation of the present invention suitable for oral administration may be in the form of individual units such as capsules, gelatin capsules, cachets, tablets, troches, or lozenges; powder or granule composition; an aqueous or non-aqueous solution or suspension; or water-in-oil or oil-in-water emulsion. Also, the drug may be administered in the form of a bolus, electuary or paste. The tablet may be made by compression or molding, optionally with one or more accessory ingredients. Compressed tablets may be prepared by compressing in a suitable machine the drug in a free-flowing form such as a powder or granules, optionally mixed with a binder, lubricant, inert diluent, preservative, surface active or dispersing agent. Molded tablets may be made by molding in a suitable machine a mixture of a suitable carrier and the powdered drug moistened with an inert liquid diluent.

Oral compositions generally include an inert diluent or an edible carrier. For the purpose of oral therapeutic administration, the active compound may be incorporated with excipients. Oral compositions prepared using a fluid carrier for use as a mouthwash may include the compound in the fluid carrier and be applied orally and swished and expectorated or swallowed. Pharmaceutically acceptable binding compounds and/or adjuvant materials may be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose; a disintegrating compound such as alginic acid, Primogel or corn starch; a lubricant such as magnesium stearate or Sterotes; a glidant such as colloidal silicon dioxide; a sweetening compound such as sucrose or saccharin; or a flavoring compound such as peppermint, methyl salicylate or organic flavoring.

Pharmaceutical compositions suitable for an injectable use include sterile aqueous solutions (where water soluble) or dispersions and sterile powder for extemporaneous preparation of sterile injectable solutions or dispersions. For intravenous administrations, suitable carriers include physiological saline, bacteriostatic water, Cremophor EL™ (BASF, Parsippany, N.J.), or phosphate buffered saline (PBS). It should be stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion and by the use of surfactants. In many cases, preferably, isotonicity agents, for example, sugars, polyalcohols such as manitol, sorbitol, or sodium chloride are included in the composition. Prolonged absorption of the injectable compositions may be performed by including in the composition an active agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

Formulations suitable for intra-articular administration may be in the form of a sterile aqueous preparation of a drug which may be in microcrystalline form, for example, in the form of an aqueous microcrystalline suspension. Liposomal formulations or biodegradable polymer systems may also be used to prepare the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface may be prepared by dispersing the drug with a dermatologically acceptable carrier such as a lotion, cream, ointment or soap. In particular, carriers capable of forming a film or layer over the skin to localize application and inhibit removal are useful. For topical administration to internal tissue surfaces, the active agent may be dispersed in a liquid tissue adhesive or other substance known to enhance adsorption to a tissue surface. For example, it is advantageous to use hydroxypropylcellulose or fibrinogen/thrombin solutions. Alternatively, tissue-coating solutions, such as pectin-containing formulations may be used.

For inhalation treatments, inhalation of powder (self-propelling or spray formulations) dispensed with a spray may use a nebulizer, or an atomizer. Such formulations may be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also may be delivered in the form of an aerosol spray from pressured container or dispenser which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and include, e.g., for transmucosal administration, detergents and bile salts. Transmucosal administration may be accomplished through the use of nasal sprays or suppositories. For transdermal administration, the active compound is formulated into ointments, salves, gels, or creams as generally known in the art.

There is no particular limit to the kind of food composition. Examples of foods include meat, sausages, bread, chocolate, candies, snack, confectionery, pizza, noodles, gums, dairy products including ice cream, various soups, beverages, teas, drinks, alcoholic beverages and multi-vitamin preparations. The health foods include all health foods in a conventional sense.

The food composition may include health beverage composition, and may additionally contain various sweetening agents or natural carbohydrates as in conventional beverages. The natural carbohydrates include monosaccharides, such as glucose and fructose, disaccharides, such as maltose and sucrose, polysaccharides, such as dextrin and cyclodextrin, and sugar alcohols, such as xylitol, sorbitol, and erythritol. Sweeteners include natural sweeteners such as thaumatin and stevia extracts, and synthetic sweeteners, such as saccharin and aspartame. The natural carbohydrates are generally used in an amount of about 0.01-0.04 g, and preferably about 0.02-0.03 g, based on 100 ml of the culture medium of adipose-derived stem cell-T (ADSC-T) cells in which T-antigen is introduced into an adipose-derived stem cell of the present invention.

The "cosmetic composition" of the present invention may be prepared in various types according to a general cosmetic preparing method using the culture medium of an adipose-derived stem cell of the present invention. For example, the cosmetic composition may be prepared in a type, such as an enterotropic product, shampoo, hair lotion, hair cream, hair gel, etc., and may be used by diluting it with cleansing solution, astringency solution, and moisturizing solution. In addition, the cosmetic composition may include general adjuvants such as stabilizer, a dissolving agent, vitamins, pigments, and a flavoring agent, which are generally used in the cosmetic composition field. For the cosmetic composition, the content of the culture medium may be included in an effective amount for achieving an effect on promoting hair growth, for example, 0.001 to 10 wt %, and preferably about 0.01 to 1 wt % with respect to the total weight of the composition.

For statistical processing of the experimental data in the example of the present invention, the difference of average of the test group and the control group was determined to be significant when p value is less than 0.05 by performing the Mann-whitney U test using the SPSS 20 program.

Hereinafter, the present invention will be described in detail with reference to Examples. However, it will be obvious to a person having ordinary skill in the art that these examples are for illustrative purposes only, and the present invention is not intended to be limited by the following Examples.

[Preparation Example 1] Preparation of Culture Medium of Adipose-Derived Stem Cell-T Cell (ADSC-T Cell) in which T-Antigen is Introduced into Adipose-Derived Stem Cell (ADSC)

1. Isolation of Adipose-Derived Stem Cell from Adipose Tissue and Culture Thereof The isolation of ADSC was performed by extracting ADSC from adipose tissues of a patient who underwent a liposuction in a plastic surgery center, after obtaining the patient consent. Specifically, the isolated adipose tissues were washed with phosphate buffered saline (PBS), mixed with 0.075% collagenase (Sigma) at a weight ratio of 1:1, and then treated at 37° C. for 45 minutes. After treatment with the enzyme, the adipose tissues were centrifuged at 800 G for 5 minutes, and the lipid and adipocyte layer that were floating on a supernatant were removed, and then filtered through a 100 μm filter to remove cellular residues. After adding normal saline solution to the filtrate, the filtrate was centrifuged at 300 G for 3 minutes and the cells were washed about 2 to 3 times, to obtain ADSC.

The obtained ADSC was cultured in Dulbecco's Modified Eagle Media (DMEM) containing 10% fetal bovine serum (FBS), 100 units/ml penicillin, and 100 μg/ml streptomycin in an incubator of 5% $CO_2$ at 37° C. The isolated ADSC was mixed with red blood cells, and in order to remove the red blood cells, a buffer for lysing the red blood cells may be used, but when the buffer for lysing the red blood cells is used, the number of ADSC tends to decrease. Therefore, at the initial stage of culture, the isolated ADSC in an original state was cultured with red blood cells. For this reason, at the initial stage of culture, ADSC was mixed with red blood cells for culture (FIG. 1A). One day after the initial culture, it was determined that ADSC was completely attached on plates, and the cells were washed with PBS twice to remove the floating cells and red blood cells. The red blood cells which were not completely removed were removed by trypsinization during subculture. When the cell confluence reached 80 to 90% of the incubator, the subculture was carried out.

About 2 to 3 days after the initial culture, it was confirmed that ADSC having fibroblast morphology was exhibited. Thereafter, after sub-culturing the cells in 10 cm plates, the shape of ADSC was observed. The results are illustrated in FIG. 1.

As illustrated in FIG. 1, it was confirmed that ADSC exhibited the same morphology as fibroblasts like other adult stem cells.

2. Confirmation on Differentiation Potency of ADSC into Adipocyte

In order to confirm whether ADSC obtained from the above experiment on isolation and culture of ADSC differentiate into adipocytes, the differentiation of ADSC was induced for 4 weeks using the medium for inducing differentiation into adipocytes, and thereafter, the differentiation of ADSC into adipocytes was confirmed. As the medium for inducing differentiation into adipocytes, Preadipocyte Differentiation Medium sold by PromoCell was used, and as a medium for maintaining the differentiated adipocytes, Adipocyte Nutrition Medium sold by PromoCell was used. Specifically, the differentiation of ADSC was induced by culturing the cells in the medium for inducing differentiation into adipocytes for 10 days while changing the medium every 3 days. Thereafter, the medium was changed to the medium for maintaining the adipocytes, and then the cells were further cultured for 20 days. The cultured cells were fixed in 10% formalin, and stained with 60% Oil-Red O solution to visualize lipid droplets in cells. The results are illustrated in FIG. 2 [(A) before induction of differentiation of ADSC, (B) 30 days after induction of differentiation, and (C) the results of staining the cells with Oil-Red O 30 days after induction of differentiation].

As illustrated in FIG. 2, 30 days after culture, lipid droplets specific to adipocytes were observed in ADSC, and thus it was confirmed that the cells were differentiated into adipocytes. Further, as a result of staining the cells with Oil-Red O 30 days after culture, the lipid droplets were stained in red, it was confirmed that the cells were differentiated into adipocytes (C). Also, it was confirmed that the cells of which differentiation was not induced were not stained (A). Therefore, it can be understood that ADSC have the differentiation potency into normal adipocytes.

3. Establishment of ADSC-T Cell Line by Expression of T Antigen of SV40 and Characteristics Thereof (1) Transfection In order to stably express T antigen of SV40 in ADSC, pEF321β-T plasmid DNA expressing T antigen of SV40 was introduced into ADSC using an electroporation. Specifically, 20 μg of the plasmid vector pEF321β-T and 1×10 ADSC were mixed in 800 μl of serum-free DMEM, and added into a 0.4 cm² cuvette. Then, an electric shock was applied thereto. The electric shock was carried out under the conditions of 160 V and 15 msec using Gene Pluser X cell Electroporation System (BIO-RAD). ADSC that form high density focus by introducing the plasmid vector pEF321β-T were trypsinized by covering a penicillin cap, and then the cells were cloned and cultured in a 24 well plate. Then, the cells were sub-cultured when the cells reached 80 to 90% of the incubator. The cell line was called ADSC-T.

The morphological changes of ADSC-T cells are illustrated in FIG. 3.

As illustrated in FIG. 3A, it was confirmed that in the case of primary ADSC, monolayer was formed by stopping the cell proliferation due to contact inhibition in the shape of fibroblasts having long and large cells. In addition, as illustrated in FIGS. 3B and 3C, it was confirmed that ADSC-T cells in which T antigen of SV40 was expressed by introducing pEF3211β-T plasmid into primary ADSC were not affected with the contact inhibition, and the cells were grown on the monolayer while overlapping each other, thereby forming high-density focus. In addition, as illustrated in FIG. 3D, it was confirmed that ADSC-T had a smaller size of cells and was changed to spindle shape. It can be estimated that the cell morphological change of ADSC-T was due to the expression of T antigen of SV40.

(2) Expression of T Antigen of ADSC-T Cell-Fluorescent Antibody Staining Method

In order to confirm the expression of T antigen in ADSC-T cells, the fluorescent antibody staining method was carried out using a monoclonal antibody to T antigen of SV40 and an anti-mouse IgG marked with fluorescein isothiocyanate (FITC), and then the expression of T antigen was observed under UV. At this time, COS-1 cells were used as a control group, and the COS-1 cells, which were prepared using T antigen of SV40, were used for comparison and confirmation on expression of T antigen of SV40 in ADSC-T cells.

Specifically, ADSC-T cells and COS-1 cells were fixed with a mixture solution where ethanol and acetone were mixed at a volume ratio of 1:1, for 18 minutes. The fixed cells were washed with PBS, and then cultured with a mice monoclonal antibody, which specifically binds to T antigen of SV40, at 37° C. for 1 hour. The cultured cells were washed with PBS, and then cultured with an anti-mouse IgG of rabbit, marked with FITC, at 37° C. for 1 hour. The cultured cells were observed with a fluorescence microscope. The results of the experiment are illustrated in FIG. 4.

As illustrated in FIG. 4, it was confirmed that ADSC-T cells isolated from high-density focus were stained with the monoclonal antibody to T antigen of SV40, and that T antigen was expressed as in the COS-1 cells.

3. Confirmation on Expression of T Antigen in ADSC-T Cell Using Western Blotting The total cell extracts from each of three ADSC-T cells were prepared, and then T antigen of SV40 present in the cells was detected using a western blotting. Specifically, the extract of each of the cells including the same amount of proteins was subjected to electrophoresis with 10% SDS-polyacrylamide gel, and then transferred to nitro cellulose membranes. After binding to mice monoclonal antibody (IgG) specifically binding to T antigen of SV40, and then the nitro cellulose membrane was colored with an anti-mouse IgG conjugated with peroxidase.

The results are illustrated in FIG. 5.

As illustrated in FIG. 5, as a result of the western blotting analysis, it was confirmed that T antigen was expressed in three ADSC-T cells (B, C, and D) as in COS-1 (E) that was used as a positive control group, and that T antigen was not expressed in the primary ADSC that was used as a negative control group (A). From these results, it can be understood that the isolated ADSC-T cell line stably expresses T antigen, that the cell proliferation increases due to T antigen, and that the cell morphology was changed.

4. Proliferation Rate of ADSC-T Cell Established by T Antigen of SV40

The cell proliferation rates between ADSC-T established by T antigen of SV40 and primary ADSC were measured and then compared. When the cell confluence reached 80% during the cell culture, the subculture was carried out and the cells were counted every passage, and the cell growth curve was prepared and then compared. The results are illustrated in FIG. 6.

As illustrated in FIG. 6, it was found that while the primary ADSC were subjected to cell division once every about 6 to 7 days, the three ADSC-T cells were subjected to cell division once every about 2 days. In addition, in the case of the primary ADSC, the proliferation rate was gradually reduced to be extinct. On the other hand, in the case of ADSC-T cells, even though there was a slight difference, the three cell lines generally showed prolonged cell lifespan and fast proliferation rate. The improvement of the proliferation rate was continuously maintained for about 6 months (50 passage), and after that, the proliferation rate of the cell was reduced.

5. Preparation of Culture Medium of ADSC-T Cells

In order to prepare the cell culture medium of the present invention, ADSC-T and ADSC were cultured for 3 days in culture media (CM) in DMEM containing 10% FBS. For the number of passage of CM used for the experiment, CM obtained from 22 passage for ADSC-T and 6 passage for the primary ADSC were used.

[Example 1] Verification of Anti-Inflammatory Effect of ADSC-T Cell Culture Medium 1. Experiment of In Vivo Anti-inflammatory Effect of ADSC-T Cell Culture Medium using C57BL/6 Mice In order to verify the anti-inflammatory effect of ADSC-T culture supernatant, C57BL/6 mice experiment was carried out.

7-week-old C57BL/6 mice were used in the mice experiment. The hairs of abdominal regions of the mice were primarily removed using an animal clipper, and secondarily, the remained hairs were completely removed using a general depilatory for about 2 to 3 minutes. Then, the hairs were completely and cleanly removed. ADSC-T was cultured in $1 \times 10^5$ cell/ml, respectively, and when 3 days passed after the cell confluence reached 80%, a culture supernatant was obtained. The obtained culture supernatant was filtered through a 0.2 filter, and the supernatant was used as a sample culture medium.

As a substance causing atopy, 1-chloro-2,4dinitrochlorobenzene (DNCB) was used, and DNCB was used after being diluted in acetone in a concentration of 0.5%. 50 μl of DNCB was applied to right and left sides of the abdominal regions for one week, and when atopic dermatitis were caused visible to the eyes, ADSC-T culture supernatant was applied from that point of time. When applying the culture supernatant, DNCB was also applied in order to avoid natural healing of the mice, with 6-hour time interval. In order to confirm the treatment effect on atopic dermatitis, the mice were subjected to light inhalation anesthetic using ether once a day and photographs were taken for investigation. One day before applying the culture supernatant on the abdominal regions of the mice where atopic dermatitis was caused was set as 0 day. The results are illustrated in FIG. 7.

As illustrated in FIG. 7, it was observed that the portions where pieces of flesh festered were peeled off in the left abdominal regions on which the culture supernatant was applied 2 days after application of the culture supernatant, and thus it can be understood that it has an anti-inflammatory effect. It was observed that the right abdominal regions on which the culture supernatant was not applied turned red, whereas almost all of the hardened discharge was peeled off from the left abdominal regions on which the culture supernatant was applied 3 days after application of the culture supernatant. As a result of comparison of red portions between the both sides 9 days after application of the culture supernatant, it was observed that the red portions of the left abdominal regions on which the culture supernatant was applied were smaller than those of the right abdominal regions on which the culture supernatant was not applied. It was confirmed that the redness in the left abdominal regions on which the culture supernatant was applied 12 days after application of the culture supernatant disappeared and thus the regions were almost cured, whereas redness was left in the right abdominal regions. As a result, it was confirmed that the culture supernatant of ADSC-T cells is effective in alleviating atopic dermatitis that is an autoimmune disease.
2. Experiment of In Vitro Anti-Inflammatory Effect of ADSC-T Cell Culture Medium Using Western Blotting In order to confirm in vitro anti-inflammatory effect of the culture supernatant of ADSC-T cells, a western blotting experiment was carried out. Plasmids expressing IκBα, Ikkβ, and NIK were transfected in 293T cells to activate NF-κB, and after 24 hours, the culture supernatant of ADSC-T cells was added to the medium, to obtain cells every 2 hours. The obtained cells were suspended with a buffer A (10 mM pH 7.9 hepes, 1 mM EDTA, 10 mM KCl, 1 mM DTT, protease inhibitor), followed by reaction on ice for 15 minutes. Thereafter, the cell membranes were destroyed by 20 times of strokes using 25 G needles in 1 ml syringes, and were centrifuged under the conditions of 14,000 rpm and 4° C. for 15 minutes, to obtain the cell culture supernatant. The isolated cell culture supernatant with required quantity of proteins was used for a western blotting. The results are illustrated in FIG. 8.

As illustrated in FIG. 8, 293T cells were transfected with the marked expressed plasmid and cultured using DMEM alone or DMEM containing 50% ADSC-T-CM. Cytoplasmic extracts were prepared to be used in the western blotting. It was confirmed that the amount of IκBα was increased in 293T cells collected every 2 hours after treatment with the culture supernatant. This means that the activity of NF-κB in the cytoplasm was decreased by the treatment with the culture medium, since IκBα is an inhibitor of NF-κB.

Further, in order to confirm the activity of NF-κB in other ways, chloramphenicol acetyltransferase assay was carried out. The results are illustrated in FIG. 9.

As illustrated in FIG. 9, it was confirmed from this experimental result that NF-κB was inhibited in 293T cells treated with the cell culture supernatant.
3. Comparison of Intracellular Expression Level of IκBα Between ADSC and ADSC-T In order to compare intracellular expression level of IκBα between ADSC and ADSC-T, ADSC and ADSC-T cells were treated with a total lysis buffer, to obtain cell extracts. The obtained cell extracts were subjected to electrophoresis, and a western blotting experiment was carried out. The results are illustrated in FIG. 10.

As illustrated in FIG. 10, it was demonstrated that the amount of IκBα was greater in ADSC-T cell extract than in ADSC extract. From the result, it can be estimated that the activity of NF-κB in ADSC-T cytoplasm was inhibited. Thus, it is estimated that no elements that may activate NF-κB are present in the culture medium culturing ADSC-T, and rather it is expected that NF-κB can be inhibited.

Thus, through the above experimental results, it was confirmed that the culture medium of ADSC-T cells of the present invention in which T-antigen was introduced into ADSC has an effect of preventing or treating an inflammatory disease.

[Example 2] Verification of Skin Regeneration and Wound Healing Effects of Culture Medium of ADSC-T Cell 1. Lattice Contraction Assay of Fibroblast-Populated Collagen In order to produce a collagen solution, 5×DMEM (—NaHCO$_3$) and a sterile reconstitution buffer (2.2 g NaHCO$_3$, 0.05 N NaOH, 200 mM HEPES in 100 ml) were prepared. A collagen type (Nitta Gelatin, Japan) 7 volume, 5×DMEM 2 volume, and buffer 1 were mixed on ice. After setting the number of cells to be $1 \times 10^5$ per well, the collagen solution was added thereto and mixed, such that bubbles were generated at the minimum. The cells were divided into 6 wells in an amount of 1.5 ml per well, followed by incubation under the conditions of 37° C. and 5% CO$_2$ for 30 minutes. The edge of the hardened collagen was cut off using a sterile syringe, and a sample medium to be treated was added thereto in a concentration of 50%, followed by incubation for 8 days. The collagen square was measured Using Image J Program.
2. Skin Contraction Effect of Culture Medium of ADSC-T in Fibroblast-Populated Collagen Lattice (FPCL) Culture Experiment 90% of the dermis is composed of collagen, and the amount of collagen in the skin is associated with moisturizing and elasticity. The healing process of a wound in the skin includes hemostasis, inflammation, proliferation, and wound contraction, and in the step of wound contraction, collagen contraction is important. This process is similar to the process of repairing skin tissue from wound and anti-aging. The effects of anti-aging (increase in elasticity) and wound contract can be confirmed from the culture medium using a fibroblast-populated collagen lattice (FPCL) model in vitro, and in the present experiment, collagen contraction was confirmed when the stem cell culture medium was treated using FPCL. Fibroblasts (3Y1) were mixed in collagen to form collagen and cultured using a medium containing the stem cell culture medium in a concentration of 50%. First, the cells in collagen were cultured for 2, 5, and 8 days and observed with a microscope. The results are illustrated in FIGS. 11 and 12.

As illustrated in FIG. 11, there was no significant difference for 2 days. However, after 2 days, it was observed that the cells in collagen treated with ADSC-T CM grew while forming networks. The results are illustrated in FIG. 12.

Also, as illustrated in FIG. 12, as a result of measuring the square of collagen 8 days after culture, the square of collagen of the control group was 9.6 cm$^2$, that of ADSC-T was 4.3 cm$^2$, and that of ADSC was 10.1 cm$^2$. The square of collagen of ASDC-T was decreased by 2.4 times, as compared with its initial square of 10.4 cm$^2$.

It can be understood that the culture medium of ADSC-T is excellent in contraction function around wounds and can be used as a raw material of functional cosmetics for skin regeneration and anti-aging and pharmaceuticals for healing wounds. The culture medium of primary ADSC (6 passage) exhibited almost no effect when compared with the control group.

3. Analysis of Wound Healing Effect of Culture Medium of ADSC-T Through Detection of Cell Migration Distance (1) In order to confirm the wound healing process, the migration distance of fibroblasts 3Y1 was detected. 3Y1 was cultured to be 100% confluence, and then the cells were lined with the width of 1600 μm (±100 μm) using a sterile tip. Thereafter, the stem cell culture medium was added thereto, and as a control group, 3Y1 culture medium was prepared in the same manner as the stem cell culture medium, in order to correct serum. The photographs of the cell migration distances were taken at 24- and 48-hour intervals, and the migration distances were measured using Image J program.

(2) Fibroblasts play the most important role in enhancing elasticity in the skin, improving wrinkles, and healing wounds. The mobility of the cells enables enhancement of skin elasticity and quick repair of wounds. In order to confirm the wound healing effect of the stem cell culture medium, the mobility of rat fibroblasts 3Y1 was confirmed. 3Y1 was cultured in 100 mm plates with confluent and lined with a sterile tip. Thereafter, the cells were treated with the culture media of ADSC-T and of primary ADSC in a concentration of 50%. 3Y1 with no treatment was used as a control group. The cell migration distances were measured at 24- and 48-hour intervals, and the images of the cells at the time of 48 hours were taken. The results are illustrated in FIG. 13.

As illustrated in FIG. 13A, it was confirmed that the cells treated with the culture medium of ADSC-T actively move at the time of 48 hours.

As illustrated in FIG. 13B, as a result of measuring the migration distances, the cells treated with ADSC-T migrated 730 μm at 24 hours and 1123 μm at 48 hours, and the cells treated with ADSC migrated 513 μm and 857 μm. The effect of the culture medium of ADSC-T cells on wound healing is higher than that of 6 passage of the culture medium of primary ADSC.

Thus, it was confirmed that the culture medium of ADSC-T cells of the present invention has significant effects of healing wounds.

4. Confirmation on Collagen Production Promotion Effect of Culture Medium of ADSC-T (1) In order to measure the amount of collagen in cells and isolated collagen, 3Y1 cells were treated with the stem cell culture medium in a concentration of 50%, followed by incubation for 5 days. The stem cell culture medium was washed with PBS twice, collected, centrifuged under the condition of 11,000 rpm for 3 minutes, to remove a supernatant, and suspended with a total lysis buffer (20 mM 7.0 Hepes, 25% Glycerol, 450 mM NaCl, 0.4 mM EDTA, 0.5 mM DTT, protease inhibitor, 1% NP-40). The medium was reacted on ice for 1 hour, and centrifuged under the conditions of 12,000 rpm and 4° C. for 15 minutes, to obtain a supernatant. For the obtained supernatant, proteins were quantified using a Bradford assay and a western blotting was carried out.

The sample proteins were subjected to electrophoresis (75 V, 2 hours) with 8% SDS-polyacrylamide gel, and then subjected to electrotransfer (90 V, 3 hours) with Hybond ECl (Amersham) membrane. Thereafter, the membrane was blocked with 5% skim milk. The membrane was reacted at room temperature for 2 hours using the primary antibody of COL1A2 (SANTA CRUZ BIOTECHNOLOGY), washed with TBS-T (tris-buffered saline-tween: pH 7.6 Tris-HCl, 137 mM NaCl, 0.1% Tween-20) solution 3 times, and reacted at room temperature for 1 hour with a peroxidase-conjugated anti-goat IgG secondary antibody. After washing with TBS-T solution 3 times, coloring with enhanced chemiluminescence (ECL), and exposing to X-ray film, the analysis thereon was carried out.

(2) The proliferation of fibroblasts and the increase of collagen production thereby during the skin wound repairing process are important elements in the skin wound repairing process. Accordingly, the stem cell culture medium was treated to 3Y1 cells, and the production of intracellular collagen protein and the amount of extracellular isolated collagen protein were confirmed from the western blotting, in comparison with the group with no treatment. The results are illustrated in FIG. 14.

As illustrated in FIG. 14, it was confirmed that intracellular collagen protein increased when treated with the culture medium of ADSC-T (FIG. 14A). Further, it was confirmed that the isolated collagen in the medium increased when compared with the group with no treatment (FIG. 14B). From the results, it can be understood that the culture medium of ADSC-T of the present invention induces wound healing and skin regeneration by promoting collagen contraction and collagen production of fibroblasts.

Thus, it was proved that the culture medium of ADSC-T of the present invention has significant effects as a raw material of wound healing agents and functional cosmetic for skin regeneration, anti-aging, and wrinkle improvement.

[Example 3] Verification of Skin Whitening Effect of Culture Medium of ADSC-T Cell 1. Confirmation on Melanin Production Inhibitory Effect of Culture Medium of ADSC-T (1) In order to measure melanin, melanoma 16F10 cells were cultured in 100 mm plates, treated with the stem cell culture medium in a concentration of 50%, and cultured for 24 hours, 48 hours, and 72 hours, respectively. The number of cells per time duration was set to $3.5 \times 10^6$ and collected, and washed with PBS. Thereafter, the cells were centrifuged under the condition of 1100 rpm for 3 minutes, to obtain cell precipitates. 1 N NaOH.DMSO solution was added to the cell pellet and the medium and subjected to vortexing, followed by treatment at 80° C. for 1 hour. Thereafter, absorbance was measured at 492 nm, and the amount of melanin was exhibited with respect to the amount of that of the group with no treatment.

(2) Mouse melanoma B16F10 cells were treated with the stem cell culture medium to confirm the inhibition of melanin production. B16F10 cells were cultured using media containing 50% culture media of ADSC-T and ADSC. Cells cultured with DMEM containing no culture medium were used as a control group. The amount of melanin produced in the cells with no treatment was compared with the amount of melanin produced when treated with the culture medium. The amounts of melanin in the cells and the media were measured at 24, 48, and 72 hours. The cells were washed with PBS and precipitated, and then the colors of cell pellets were identified with a digital camera. The results are illustrated in FIG. 15.

As illustrated in FIG. 15, it was confirmed that the melanin production was noticeably inhibited from 48 hours in the cell precipitates of B16F10 treated with the culture medium of ADSC-T and that the color of cell pellet was distinguished. Further, in the case of the cells cultured for 72 hours, the difference in melanin production was much more remarkable.

Further, B16F10 cell pellets of $3 \times 10^5$ were treated with 1 N NaOH.DMSO and the cells were melted at 80° C. The amount of melanin therein was measured at 492 nm. The results are illustrated in FIG. 16.

As illustrated in FIG. 16, it was confirmed that the amount of melanin at 72 hours after being treated with the culture medium of ADSC-T was reduced down to 73% when compared with the group with no treatment (FIG. 16A). In order to measure melanin released from B16F10 cells, the media collected at each time intervals were measured according to the above method. As a result, it was confirmed that there was no difference in the amounts of melanin in the media treated with the culture medium of primary ADSC, and that when compared with melanin in the media treated with the culture medium of ADSC-T, the amounts of melanin were 83.9%, 76.1%, and 50.5%, respectively, which were reduced as times went (FIG. 16B).

2. Verification of Tyrosinase Activity Inhibitory Effect of Culture Medium of ADSC-T (1) B16F10 cells were cultured and 50% stem cell culture medium was added thereto, followed by incubation for 48 and 72 hours. Thereafter, the cells were washed with PBS twice and centrifuged at 1100 rpm for 8 minutes, to obtain cells. A lysis buffer (20 mM sodium phosphate, pH 6.8, 1% Trion x-100, 1 mM protein inhibition) 800 µl was added and vortexing was repeated 5 times for 10 seconds. A culture supernatant obtained from centrifugation for 15 minutes under the conditions of 12000 rpm and 4° C. was used as a tyrosinase enzyme liquid. For the enzyme liquid, proteins were quantified using a Bradford assay, and the same amount was used. In order to confirm tyrosinase activity, 2.5 mM L-3,4-Dihydroxy-L-phenylalanine (DOPA, Sigma-Aldrich), 50 mM phosphate buffer (pH 6.8) and the enzyme liquid were added, followed by reaction at 37° C. for 20 minutes. The absorbance was measured at 475 nm. The tyrosinase activity was indicated with respect to that of the group with no treatment.

(2) The effect inhibited when the produced amount of melanin was treated with the culture medium of ADSC-T was confirmed. Tyrosinase is the most important enzyme for melanin production process and involved in melanin formation from a first step. Therefore, in order to confirm melanin production inhibitory activity of the culture medium of ADSC-T again, the activity inhibition on tyrosinase by the culture medium of ADSC-T was examined.

In order to measure tyrosinase activity, B16F10 cells were treated with the culture medium in a concentration of 50% and collected 48 hours after the treatment, and a buffer was added thereto, to obtain intracellular proteins. The solution was used for measuring tyrosinase activity. Tyrosinase proteins were quantified using a Bradford assay, and the same amount of proteins was obtained to measure absorbance at 475 nm for the level of L-dopa becoming dopachrome. The results are illustrated in FIG. 17.

As illustrated in FIG. 17, tyrosinase activity of the culture medium of ADSC-T was 26.5%, and that of the culture medium of primary ADSC was 84.9%, when compared with tyrosinase activity of the group with no treatment. Thus, it was confirmed that the culture media of ADSC-T and ADSC inhibited tyrosinase, and that the inhibitory effect was greater in the culture medium of ADSC-T than in the culture medium of ADSC.

Thus, it was confirmed that the culture medium of ADSC-T of the present invention inhibits tyrosinase activity and reduces melanin synthesis, and thereby exhibits whitening effect.

[Example 4] Verification of Anti-Oxidation Effect of Culture Medium of ADSC-T Cell Through DPPH Assay (1) Anti-oxidation effect of the stem cell culture medium was confirmed from 2,2-diphenyl-1-picrylhydrazyl (DPPH) radical scavenging activity. 0.13 mM DPPH (2,2-Diphenyl-1-picrylhydrazyl, Sigma-Aldrich) solution was prepared in ethanol, and 0.13 mM DPPH and the sample were mixed at a weight ratio of 1:1 and reacted in dark room for 10 and 20 minutes. The decrease of absorbance at 515 nm was confirmed.

$$DPPH \text{ radical scavenging activity } (\%) = \left[ \frac{Abs_{control} - Abs_{sample}}{Abs_{control}} \right] \times 100$$

Abs Control: Group with No Treatment
Abs Sample: Group with Treatment (2) In order to confirm the anti-oxidation effect of the stem cell culture medium, DPPH assay was used. DPPH, which is a very stable free radical itself, is a violet compound exhibiting the optical absorption at 515 nm. DPPH is decolored by proton-radical scavenger and becomes yellow, and thus it can be observed with naked eyes. After preparing 0.13 mM DPPH solution, a decrease of absorbance was investigated when treated with the culture medium of ADSC-T. The culture medium of ADSC-T was mixed with 0.13 mM DPPH solution at a weight ratio of 1:1 and reacted in dark room for 10 and 20 minutes. A decrease of absorbance at 515 nm was confirmed. The stem cell culture medium is produced from DMEM medium in which vitamin E with antioxidant activity is contained, and thus it is expected to scavenge DPPH radical. Accordingly, the experiment was carried out in comparison with the DMEM medium. The results are illustrated in FIG. 18.

As illustrated in FIG. 18, the DMEM medium itself scavenges DPPH radical but the scavenging activity was reduced 20 minutes after addition of the medium. It means that the amount of substances scavenging DPPH radical in the medium is insignificant. The culture medium of ADSC-T exhibited higher scavenging capacity than the DMEM medium from the reaction after 10 minutes, and showed much higher scavenging activity when reaction for 20 minutes. In comparison with the DMEM medium, the culture medium of ADSC-T inhibited DPPH radical about a twofold than the DMEM medium.

Thus, it was confirmed that the culture medium of ADSC-T of the present invention exhibited remarkable anti-oxidation effect.

Hereinafter, preparation examples of the pharmaceutical composition, food composition, and cosmetic composition of the present invention are described for illustrative purposes only, and the present invention is not intended to be limited by the following preparation examples.

Formation Example 1. Preparation of Pharmaceutical Formation 1-1. Preparation of Powder Formation
Culture medium of ADSC-T cell 20 mg
Lactose 100 mg
Talc 10 mg The above ingredients are mixed and filled into a sealed pouch to prepare a powder formulation.

1-2. Preparation of Tablet Formation
Culture medium of ADSC-T cell 10 mg
Cornstarch 100 mg
Lactose 100 mg
Stearic acid magnesium 2 mg The above ingredients are mixed, and then tabulated according to a general tablet preparation method to prepare a tablet formulation.

1-3. Preparation of Capsule Formulation
Culture medium of ADSC-T cell 10 mg
Crystalline cellulose 3 mg
Lactose 14.8 mg
Magnesium stearate 0.2 mg The above ingredients are mixed, and then filled into a gelatin capsule according to a general capsule preparation method to prepare a capsule formulation.

1-4. Preparation of Injection Formulation
Culture medium of ADSC-T cell 10 mg
Mannitol 180 mg
Sterile distilled water for injection 2974 mg
$Na_2HPO_4 \cdot 2H_2O$ 26 mg An injection formulation is prepared with the above ingredient amounts per ample (2 ml) according to a general injection preparation.

1-5. Preparation of Liquid Formulation
Culture medium of ADSC-T cell 20 mg
Isomerized glucose syrup 10 g
Mannitol 5 g
Purified water q.s.

According to a general liquid preparation method, each ingredient is added to purified water to be dissolved therein, proper quantity of lemon flavor is added thereto, and then the ingredients are mixed. Purified water is added to the mixture so as to be 100 ml in total and filled into a brown bottle and sterilized to prepare a liquid formulation.

Formulation Example 2

Preparation of Food Formulation 2-1. Preparation of Health Care Food
Culture medium of ADSC-T cell 100 mg
Vitamin mixture proper quantity
Vitamin A acetate 70 µg
Vitamin E 1.0 mg
Vitamin B1 0.13 mg
Vitamin B2 0.15 mg
Vitamin B6 0.5 mg
Vitamin B12 0.2 µg
Vitamin C 10 mg
Biotin 10 µg
Nicotinic acid amide 1.7 mg
Folic acid 50 µg
Pantothennic acid calcium 0.5 mg
Mineral mixture q.s.
Ferrous sulfate 1.75 mg
Zinc oxide 0.82 mg
Magnesium carbonate 25.3 mg
Potassium phosphate monobasic 15 mg
Calcium phosphate dibasic 55 mg
Potassium citrate 90 mg
Calcium carbonate 100 mg
Magnesium chloride 24.8 mg The above ratio of vitamin and mineral mixtures illustrates a preferred example of mixing the ingredients relatively appropriate for a health care food, but it may be arbitrarily modified. According to a general health care food preparation method, the above ingredients are mixed to prepare granules, and the granules may be used for the preparation of a health care food composition according to a general method.

2-2. Preparation of Health Care Beverage
Culture medium of ADSC-T cell 100 mg
Vitamin C 15 g
Vitamin E (powder) 100 g
Ferrous lactate 19.75 g
Zinc oxide 3.5 g
Nicotinic acid amide 3.5 g
Vitamin A 0.2 g
Vitamin B1 0.25 g
Vitamin B2 0.3 g
Water q.s.

According to a general health care beverage preparation method, the above ingredients are mixed, heated while stirring at 85° C. for about 1 hour, and the prepared solution is filtered, filled into 2 L sterile container for sealing and sterilization, kept under refrigeration, and then used for preparing a health beverage composition of the present invention.

The above ratio illustrates a preferred example of mixing ingredients relatively appropriate for a beverage, but it may be arbitrarily modified according to regional and national preferences such as demand classes, demand nations, uses, and the like.

Formulation Example 3

Preparation of Cosmetic Formulation

1. Skin Softener
Culture medium of ADSC-T cell 0.5 wt %
Glycerin 5.0 wt %
1,3-butylene glycol 3.0 wt %
Ethanol 5.0 wt %
Polyoxyethylene nonylphenyl ether 0.5 wt %
Fragrance q.s.
Preservative q.s.
Purified water Balance 2. Skin Toner
Culture medium of ADSC-T cell 0.5 wt %
Glycerin 3.0 wt %
Citric acid 0.1 wt %
Ethanol 10.0 wt %
Polyoxyethylene oleyl ether 1.0 wt %
Sorbitol 2.0 wt %
Fragrance q.s.
Preservative q.s.
Purified water Balance 3. Lotion (Emulsion)
Culture medium of ADSC-T cell 0.5 wt %
Glycerin 3.0 wt %
1,3-butylene glycol 8.0 wt %
Squalane 10.0 wt %
Polyoxyethylene sorbitan mono-oleate 2.0 wt %
Triethanolamine 1.5 wt %
Glyceryl stearate 0.5 wt %
Stearyl glycyrrhetinate 0.2 wt %
Carboxyvinylpolymer 0.1 wt %
Arginine 0.1 wt %
Fragrance q.s.
Preservative q.s.
Purified water Balance 4. Cream
Culture medium of ADSC-T cell 0.5 wt %
Glycerin 3.0 wt %
Stearic acid 8.0 wt %
Squalane 5.0 wt %
Glyceryl mono stearic acid selfemulsifying 2.5 wt %
Polyoxyethylene sorbitan mono stearic acid 1.5 wt %
Propylene glycol 4.0 wt %
Stearyl glycyrrhetinate 0.2 wt %
Vaseline 2.0 wt %
Antioxidant q.s.
Fragrance q.s.
Preservative q.s.
Purified water Balance

What is claimed is:

1. A method for treating an inflammatory disease in a subject in need thereof, comprising administering to the subject a culture medium of adipose-derived stem cell-T (ADSC-T) cells in which T-antigen is introduced into an adipose-derived stem cell as an active ingredient.

2. The method of claim 1, wherein the T-antigen is introduced through transfection.

3. The method of claim 1, wherein the T-antigen is derived from Simian virus40 (SV40).

4. The method of claim 1, wherein the culture medium of the ADSC-T cell is prepared by a method comprising:
    (a) culturing the adipose-derived stem cells, where the adipose-derived stem cells were isolated through a centrifuge after treating an enzyme, collagenase, to a suctioned adipose tissue;
    (b) preparing the ADSC-T cells expressing a T antigen of SV40 by transfecting a plasmid expression vector into the adipose-derived stem cell cultured in the above step (a); and
    (c) obtaining a culture medium by culturing the ADSC-T cells prepared in the above step (b).

5. The method of claim 4, wherein the transfection in the above step (b) is carried out by at least one method selected from the group consisting of calcium phosphate transfection, electroporation, microinjection and liposome injection.

6. The method of claim 1, wherein the inflammatory disease is selected from the group consisting of allergic disease, atopic dermatitis, nasitis, asthma, acute pain, chronic pain, paradentitis, gingivitis, inflammatory bowel disease, gout, myocardial infarction, arteriosclerosis, congestive heart failure, hypertension, angina pectoris, stomach ulcer, Alzheimer's disease, cerebral infarction, Down's syndrome, multiple sclerosis, obesity, diabetes, dementia, depression, schizophrenia, tuberculosis, sleep disorder, sepsis, a burn, and pancreatitis.

7. A method for improving skin-regeneration in a subject in need thereof, comprising administering to the subject a culture medium of ADSC-T cells in which T-antigen is introduced into an adipose-derived stem cell as an active ingredient.

8. A method for skin-whitening in a subject in need thereof, comprising administering to the subject a culture medium of ADSC-T cells in which T-antigen is introduced into an adipose-derived stem cell as an active ingredient.

9. A method of promoting antioxidant activity or suppressing skin aging in a subject in need thereof comprising administering to the subject a culture medium of ADSC-T cells in which T-antigen is introduced into an adipose-derived stem cell as an active ingredient.

10. A method for promoting wound-healing in a subject in need thereof, comprising administering to the subject a culture medium of ADSC-T cells in which T-antigen is introduced into an adipose-derived stem cell as an active ingredient.

* * * * *